(12) United States Patent
Ågerstam et al.

(10) Patent No.: US 10,752,692 B2
(45) Date of Patent: Aug. 25, 2020

(54) ANTI HUMAN INTERLEUKIN-1 RECEPTOR ACCESSORY PROTEIN (IL1 RAP) ANTIBODIES AND USES THEREOF

(71) Applicant: CANTARGIA AB, Lund (SE)

(72) Inventors: Helena Ågerstam, Lund (SE); Thoas Fioretos, Lund (SE); Marcus Järås, Lund (SE); Cecilia Ann-Christin Malmborg Hager, Helsingborg (SE); Kjell Sjöström, Lund (SE); Agneta Svedberg, Lund (SE); Karin von Wachenfeldt, Lund (SE)

(73) Assignee: Cantargia AB, Lund (SE)

( * ) Notice: Subject to any disclaimer, the term of this patent is extended or adjusted under 35 U.S.C. 154(b) by 0 days.

(21) Appl. No.: 16/358,459

(22) Filed: Mar. 19, 2019

(65) Prior Publication Data

US 2019/0202924 A1 Jul. 4, 2019

Related U.S. Application Data

(60) Continuation of application No. 15/707,593, filed on Sep. 18, 2017, now Pat. No. 10,287,357, which is a division of application No. 15/255,585, filed on Sep. 2, 2016, now Pat. No. 9,796,783, which is a continuation of application No. PCT/GB2015/050647, filed on Mar. 5, 2015.

(30) Foreign Application Priority Data

Mar. 5, 2014 (GB) .................... 1403875.6

(51) Int. Cl.
C07K 16/28 (2006.01)
C07K 16/30 (2006.01)
G01N 33/574 (2006.01)
A61K 39/00 (2006.01)

(52) U.S. Cl.
CPC .......... *C07K 16/2866* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3053* (2013.01); *C07K 16/3069* (2013.01); *G01N 33/57492* (2013.01); *A61K 2039/505* (2013.01); *C07K 2317/24* (2013.01); *C07K 2317/32* (2013.01); *C07K 2317/33* (2013.01); *C07K 2317/41* (2013.01); *C07K 2317/55* (2013.01); *C07K 2317/56* (2013.01); *C07K 2317/565* (2013.01); *C07K 2317/72* (2013.01); *C07K 2317/732* (2013.01); *C07K 2317/76* (2013.01); *C07K 2317/77* (2013.01); *C07K 2317/92* (2013.01); *G01N 2333/7155* (2013.01)

(58) Field of Classification Search
None
See application file for complete search history.

(56) References Cited

U.S. PATENT DOCUMENTS

| 4,235,871 A | 11/1980 | Papahadjopoulos et al. |
| 4,816,567 A | 3/1989 | Cabilly et al. |
| 5,851,451 A | 12/1998 | Takechi et al. |
| 7,960,512 B2 | 6/2011 | Stavenhagen et al. |
| 9,403,906 B2 | 8/2016 | Fioretos et al. |
| 9,458,237 B2 | 10/2016 | Fioretos et al. |
| 2003/0215453 A1 | 11/2003 | Dedera et al. |
| 2006/0019256 A1 | 1/2006 | Clarke et al. |
| 2017/0121420 A1 | 5/2017 | Heidrich et al. |

FOREIGN PATENT DOCUMENTS

| EP | 0213303 B1 | 9/1991 |
| EP | 2213683 B1 | 6/2013 |
| EP | 2467403 B1 | 10/2015 |
| EP | 2665749 B1 | 1/2016 |
| WO | 1996023067 A1 | 8/1996 |
| WO | 2005007197 A3 | 3/2005 |
| WO | 2009091547 A1 | 7/2009 |
| WO | 2009120903 A9 | 2/2010 |
| WO | 2011021014 A3 | 6/2011 |
| WO | 2012098407 A1 | 7/2012 |
| WO | 2013059973 A1 | 5/2013 |
| WO | 2016020502 A1 | 2/2016 |
| WO | 2016207304 A2 | 12/2016 |
| WO | 2017079121 A2 | 5/2017 |

OTHER PUBLICATIONS

Angov, Evelina "Codon usage: Nature's roadmap to expression and folding of proteins", Biotechnol. J. 2011, 6, 650-659.
Arndt et al., "Protein Engineering Protocols", Methods in Molecular Biology, 2007.
Askmyr et al., "Selective killing of candidate AML stem cells by antibody targeting of IL1RAP", Blood, May 2, 2013 x vol. 121, No. 18 3709-3713.
Attucci et al., "EPI-hNE4, a Proteolysis-Resistant Inhibitor of Human Neutrophil Elastase and Potential Anti-Inflammatory Drug forTreating Cystic Fibrosis", The Journal of Pharmacology and Experimental Therapeutics vol. 318, No. 2, 803-809, 2006.
Balagurunathan et al. "Gene expression progfilling based identification of cell surface targets for developing multimeric ligands in pancreatic cancer" Mol Cancer Ther. Sep. 2008, 7(9): 3071-3080.

(Continued)

*Primary Examiner* — Elly-Gerald Stoica
(74) *Attorney, Agent, or Firm* — McNeill Baur PLLC

(57) ABSTRACT

The present invention provides an antibody or an antigen-binding fragment thereof with binding specificity for human interleukin-1 receptor accessory protein (IL1RAP) wherein the antibody or antigen-binding fragment is capable of inhibiting the binding of antibody 'CAN04' to human IL1RAP. The invention further provides the use of such antibodies or an antigen-binding fragments in the treatment and/or diagnosis of IL-1 associated diseases and conditions, including cancers such as acute myeloid leukemia and melanoma.

17 Claims, 13 Drawing Sheets

Figure 1:
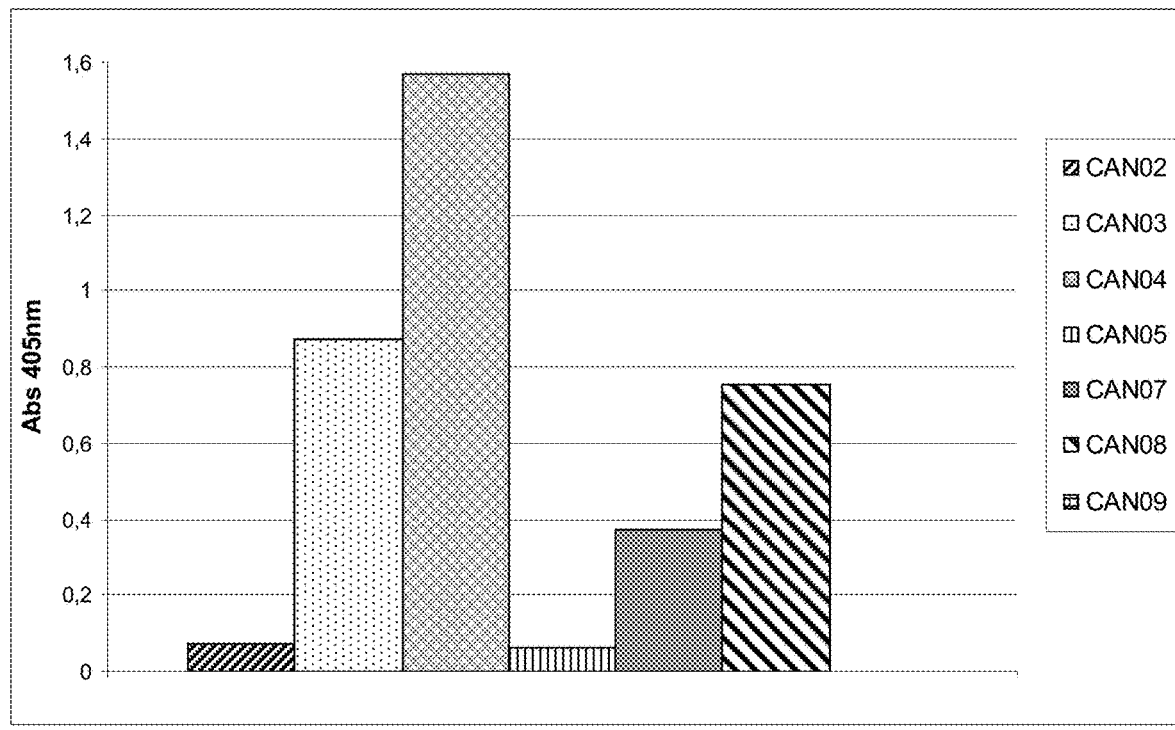

Specification includes a Sequence Listing.

(56) References Cited

OTHER PUBLICATIONS

Barreyro et al., "Overexpression of IL-1 receptor accessory protein in stem and progenitor cells and outcome correlation inAMLand MDS", Blood, Aug. 9, 2012 vol. 120, No. 6, 1290-1298.

Baudys et al., "Extending Insulin Action in Vivo by Conjugation to Carboxymethyl Dextran", Bioconjugate Chem. 1998, 9, 176-183.

Ben-Kasus et al. "Cancer therapeutic antibodies come of age: Targeting minimal residual disease" Molecular Oncology, 1, 2007, 42-54.

Binz et al., "High-affinity binders selected from designed ankyrin repeat protein libraries", Nature Biotechnology vol. 22 No. 5 May 2004, 575-582.

Boerner et al., "Production of Antigen-Specific Human Monoclonal Antibodies From In Vitro-Primed Human Splenocytes", The Journal of Immunology, vol. 147. 86-95. No. 1. Jul. 1, 1991, 86-95.

Bowen et al., "Relationship between molecular massand duration of activity of polyethylene glycol conjugated granulocyte colony-stimulating factor mutein", Experimental Hematology 27 (1999) 425-432.

Brendel, C. and Neubauer. A., "Characteristics and analysis of normal and leukemic stem cells:current concepts and future directions" Leukemia, 14:1711-1717 (2000).

Bruhns et al., "Specificity and affinity of human Fc receptors and their polymorphic variants for human IgG subclasses", Blood, Apr. 16, 2009 vol. 113, No. 16, 3716-3725.

Busfield et al., "Targeting of acute myeloid leukemia in vitro and in vivo with an anti-CD123 mAb engineered for optimal ADCC", Leukemia (2014) 28, 2213-2221.

Chamat et al., "Human Monoclonal Antibodies Isolated from Spontaneous Epstein-Barr Virus—Transformed Tumors of Hu-SPL-SCID Mice and Specific for Fusion Protein Display Broad Neutralizing Activity Toward Respiratory Syncytial Virus", JID 1999;180 (August), 268-277.

Chan et al., "Lowering of Trichosanthin Immunogenicity by Site-Specific Coupling to Dextran", Biochemical Pharmacology, vol. 57, pp. 927-934, 1999.

Chapman "PEGylated antibodies and antibody fragments for improved therapy: a review" Advanced drug delivery reviews 54 (2002) 531-545.

Chapman et al., "Therapeutic antibody fragments with prolonged in vivo half-lives", Nature Biotechnology vol. 17 Aug. 1999, 780-783.

Cole et al., "Human monoclona/antibodies", Molecular and Cellular Biochemistry 62, 109-120 (1984), 109-120.

Cote et al., "Generation of human monoclonal antibodies reactive with cellular antigens", Proc. Nati. Acad. Sci. USA, vol. 80, Apr. 1983, pp. 2026-2030.

Datta-Mannan et al., "Humanized IgG1 Variants with Differential Binding Properties to the Neonatal Fc Receptor: Relationship to Pharmacokinetics in Mice and Primates", Drug Metabolism and Disposition vol. 35, No. 1, DMD 35:86-94, 2006.

Declaration by Dr. John C. Matese, Jun. 21, 2016.

Diehn et al. "SOURCE: a unified genomic resource of funtional annotations, ontologies, and gene expression data" Nucleic Acids Research, 2003, vol. 31, No. 1.

Dinarello, Charles A. "Biologic Basis for Interleukin-I in Disease", Blood, vol. 87, No. 6 (Mar. 15), 1996: pp. 2095-2147.

Dinarello, Charles A. "Impact of basic research on tomorrow's medicine", Chest / 118 / 2 / Aug. 2000 503-508.

Dinarello, Charles Anthony "An Expanding Role for Interleukin-1 Blockade from Gout to Cancer", Mol Med 20 (Supplemental 1), S43-S58, 2014.

Edelman et al., "The Covalent Structure of an Entire TG Immunoglobulin Molecule*", vol. 63, 1969, Biochemistry,78-85.

Elliott et al., "Enhancement of therapeutic protein in vivo activities through glycoengineering", nature biotechnology, vol. 21, Apr. 2003, 414-421.

Gal, H. et al. "Gene expression profiles of AML derived stem cells; similarity to hematopoietic stem cells" Leukemia, 20:2147-2154 (2006).

Garlanda et al., "The Interleukin-1 Family: Back to the Future", Immunity 39, Dec. 12, 2013, 1003-1018.

Gebauer et al., "Engineered protein scaffolds as next-generation antibody therapeutics", Current Opinion in Chemical Biology 2009, 13:245-255.

Goldenberg, Marvin M. "Etanercept, a Novel Drug for the Treatment of Patients with Severe, Active Rheumatoid Arthritis", Clinical Therapeuticsv vol. 21, No. 1, 1999, 75-87.

Green and Sambrook., "Molecular Cloning, A Laboratory Manual", Fourth Edition, vol. 1, 2012.

Hamilton-Wessler et al., "Mechanism of protracted metabolic effects of fatty acid acylated insulin, NN304, in dogs: retention of NN304 by albumin", Diabetologia (1999) 42: 1254±1263.

Hey et al., "Artificial, non-antibody binding proteins for pharmaceutical and industrial applications", Trends in Biotechnology vol. 23 No. 10 Oct. 2005, 514-522.

Hinton et al., "Engineered Human IgG Antibodies with Longer Serum Half-lives in Primates", The Journal of Biological Chemistry, vol. 279, No. 8, Issue of Feb. 20, pp. 6213-6216, 2004.

Hoogenboom and Winter, "By-passing Immunisation Human Antibodies from Synthetic Repertoires of Germline VH Gene Segments Rearranged in Vitro", J. Mol. Hid. (1992) 227. 381-:388.

Huang and Miller, "A Time-Efficient, Linear-Space Local Similarity Algorithm", Advances in Applied Mathematics 12, 337-357 (1991).

Huang et al., "Recruitment of IRAK to the interleukin 1 receptor complex requires interleukin 1 receptor accessory protein", Proc. Natl. Acad. Sci. USA, vol. 94, Nov. 1997, pp. 12829-12832.

Iannello and Ahmad. "Role of antibody-dependent cell-mediated cytotoxicity in the efficacy of therapeutic anti-cancer monoclonal antibodies" Cancer and Metastasis Reviews, 24: 487-499, 2005.

Idusogie et al., "Mapping of the C1q Binding Site on Rituxan, a Chimeric Antibody with a Human IgG1 Fc", Immunol 2000; 164:Nov. 10, 2016, 4178-4184.

Iida et al., "Two mechanisms of the enhanced antibody-dependent cellular cytotoxicity (ADCC) efficacy of non-fucosylated therapeutic antibodies in human blood", BMC Cancer, Feb. 18, 2009, 1-12.

Järås et al. "Isolation and killing of candidate chronic myeloid leukemia stem cells by antibody targeting of IL-1 receptor accessory protein" PNAS, Sep. 14, 2010, vol. 107, No. 37, 16280-16285.

Jiang, X. et al. "Chronic myeloid leukemia stem cells possess multiple unique features of resistance to BCR-ABL targeted therapies" Leukemia, 21:926-935 (2007).

Jones et al., "Replacing the complementarity-determining regions in a human antibodywith those from a mouse"; Nature, vol. 321, May 29, 1986, 522-525.

Juric et al. "Differential gene expression patterns and interaction networks in BCR-ABL-positive and negative adult acute lymphoblastic leukemias" J Clin Oncol, 25: 1341-1349.

Köhler et al., "Continuous cultures of fused cells secreting antibody of predefined specificity", Nature, vol. 256, Aug. 7, 1975, 495-497.

Kozbor et al., "Specific Immunoglobulin Production and Enhanced Tumorigenicity Following Ascites Growth of Human Hybridomas", Journal of Immunological Methods, 81 (1985) 31-42.

Krause et al., "Grafting of thrombopoietin-mimetic peptides into cystine knot miniproteins yields high-affinity thrombopoietin antagonists and agonists", FEBS Journal 274 (2007) 86-95.

Kurtzhals et al., "Albumin binding of insulins acylated with fatty acids: characterization of the ligand-protein interaction and correlation between binding affinity andtiming of the insulin effect in vivo", Biochem. J. (1995) 312, 725-731.

Labrijn et al., "Therapeutic IgG4 antibodies engage in Fab-arm exchange with endogenous human IgG4 in vivo", nature biotechnology vol. 27 No. 8 Aug. 2009, 767-771.

Lazar et al., "Engineered antibody Fc variants with enhanced effector function", PNAS Mar. 14, 2006 vol. 103 No. 11, 4005-4010.

Majeti, R. et al. "CD47 Is an Adverse Prognostic Factor and Therapeutic Antibody Target on Human Acute Myeloid Leukemia Stem Cells" Cell, 138:286-299 (2009).

Marks et al., "By-passing Immunization Human Antibodies from V-gene Libraries Displayed on Phage", J. Mol. Biol. (1991) 222, 581-597.

(56) References Cited

OTHER PUBLICATIONS

Mézière et al., "In vivo T helper cell response to retro-inverso peptidomimetics", J Immunol 1997; 159:3230-3237.

NCBI, NCBI GEO Talatov. Host: NCBI Gene Expression Omnibus (GEO) database, Aug. 25, 2005, Jun. 21, 2016.

Nygren, Per-Åke "Alternative binding proteins: Athbody binding proteins developed from a small three-helix bundle scaffold", FEBS Journal 275 (2008) 2668-2676.

Okazaki et al., "Fucose Depletion from Human IgG1 Oligosaccharide Enhances Binding Enthalpy and Association Rate Between IgG1 and FcgRIIIa", J. Mol. Biol. (2004) 336, 1239-1249.

Orlandi et al., "Cloning immunoglobulin variable domains for expression by the polymerase chain reaction", Proc. Natl. Acad. Sci. USA, vol. 86, May 1989, pp. 3833-3837.

Osborn et al., "Pharmacokinetic and Pharmacodynamic Studies of a Human Serum Albumin-Interferon-Fusion Protein in Cynomolgus Monkeys", The Journal of Pharmacology and Experimental Therapeutics vol. 303, No. 2, 540-548 (2002).

Peipp et al., "Antibody fucosylation differentially impacts cytotoxicity mediated by NK and PMN effector cells", Blood, Sep. 15, 2008, vol. 112, No. 6, 2390-2399.

Richards et al., "Optimization of antibody binding to Fc;RIIa enhances macrophage phagocytosis of tumor cells", Mol Cancer Ther 2008;7(8). Aug. 2008, 2517-2527.

Ridker et al., "Interleukin-1β inhibition and the prevention of recurrent cardiovascular events: Rationale and Design of the Canakinumab Anti-inflammatory Thrombosis Outcomes Study (CANTOS)", American Heart Journal Oct. 2011, 597-605.

Riechmann et al., "Reshaping human antibodies for therapy", Nature, vol. 332, Mar. 24, 1988, 323-327.

Ryan et al., "Antibody targeting of B-cell maturation antigen on malignant plasma cells", Mol Cancer Ther 2007;6(11). Nov. 2007, 3009-3018.

Schlehuber and Skerra, "Keynote review: Lipocalins in drug discovery:from natural ligand-binding proteins to anticalins", DDT • vol. 10, No. 1 • Jan. 2005, 23-33.

Shields et al., "High Resolution Mapping of the Binding Site on Human IgG1 for FcgRI, FcgRII, FcgRIII, and FcRn and Design of IgG1 Variants with Improved Binding to the FcgR*", The Journal of Biological Chemistry vol. 276, No. 9, Issue of Mar. 2, pp. 6591-6604, 2001.

Silverman et al., "Multivalent avimer proteins evolved by exon shuffling of a family of human receptor domains", Nature Biotechnology, vol. 23 No. 12 Dec. 2005, 1556-1561.

Stanford University, Source Su. Host: Source Search, Dec. 31, 2009, Jun. 21, 2016.

Steurer et al., "Ex vivo coating of islet cell allografts with murine CTLA4/Fc promotes graft tolerance", J Immunol 1995; 155:1165-1174.

Strohl, William R. "Optimization of Fc-mediated effector functions of monoclonal antibodies", Current Opinion in Biotechnology 2009, 20:685-691.

Su et al. "Molecular classification of human carcinomasby use of gene expression signatures" Cancer Research 61, 7388-7393, Oct. 5, 2001.

Talantov et al. "Novel genes associated with malignant melanoma but not benign melanocytic lesions" Clin Cancer Res. 2005; 11(20) Oct. 15, 2005.

Vaccaro et al., "Engineering the Fc region of immunoglobulin G to modulate in vivo antibody levels", Nature Biotechnology vol. 23 No. 10 Oct. 2005,1283-1288.

Verhoeyen et al., "Reshaping Human Antibodies: Grafting an Antilysozyme Activity", Science, New Series, vol. 239, No. 4847 (Mar. 25, 1988), pp. 1534-1536.

Vigne et al., "IL-36 signaling amplifies Th1 responses by enhancing proliferation and Th1 polarization of naive CD4 T cells", Blood, Oct. 25, 2012 vol. 120, No. 17, 3478-3487.

Visvader et al., "Cancer stem cells in solid tumours:accumulating evidence and unresolved questions", Nature Reviews, Cancer, vol. 8, Oct. 2008, 755-768.

Von Mehren et al. "Monoclonal antibody therapy for cancer" Annu. Rev. Med. 2003, 54: 343-69.

Wang et al., "Structural insights into the assembly and activation of IL-1b with its receptors", nature immunology vol. 11 No. 10 Oct. 2010, 905-911.

Winter and Milstein, "Man-made antibodies", Nature, vol. 349, Jan. 24, 1991, 293-299.

Zalevsky et al., "Enhanced antibody half-life improves in vivo activity", nature biotechnology vol. 28 No. 2 Feb. 2010, 157-159.

SEQUENCE LISTING

<160> NUMBER OF SEQ ID NOS: 19

<210> SEQ ID NO 1
<211> LENGTH: 117
<212> TYPE: PRT
<213> ORGANISM: Artificial Sequence
<220> FEATURE:
<223> OTHER INFORMATION: Murine derived antibody sequence

<400> SEQUENCE: 1

Gln Val Gln Leu Gln Gln Ser Gly Pro Glu Leu Leu Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asn Thr His Tyr Ser Gly Lys Phe
    50                  55                  60

Lys Gly Lys Ala Thr Leu Thr Ala Asp Lys Ser Ser Ile Ala Tyr
65                  70                  75                  80

Met Gln Leu Ser Ser Leu Thr Ser Glu Asp Ser Ala Val Tyr Phe Cys
                85                  90                  95

Gly Glu Gly Tyr Leu Asp Pro Met Asp Tyr Trp Gly Gln Gly Thr Ser
            100                 105                 110

Val Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: Murine derived antibody sequence

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Lys Leu Leu Ile
        35                  40                  45

His Tyr Thr Ser Gly Leu His Ala Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Leu Glu Ile Lys Arg
            100                 105

<210> SEQ ID NO 3
<211> LENGTH: 7
<212> TYPE: PRT
<213> ORGANISM: Artificial Sequence
<220> FEATURE:
<223> OTHER INFORMATION: Murine derived antibody sequence

```
<400> SEQUENCE: 3

Gly Tyr Ala Phe Ser Ser Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Murine derived antibody sequence

<400> SEQUENCE: 4

Tyr Pro Gly Asp Gly Asn
1               5

<210> SEQ ID NO 5
<211> LENGTH: 8
<212> TYPE: PRT
<213> ORGANISM: Artificial Sequence
<220> FEATURE:
<223> OTHER INFORMATION: Murine derived antibody sequence

<400> SEQUENCE: 5

Gly Tyr Leu Asp Pro Met Asp Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: Murine derived antibody sequence

<400> SEQUENCE: 6

Gly Tyr Ala Phe Ser Ser Ser Trp Met Asn
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Murine derived antibody sequence

<400> SEQUENCE: 7

Arg Ile Tyr Pro Gly Asp Gly Asn Thr His Tyr Ser Gly Lys Phe Lys
1               5                   10                  15

Gly

<210> SEQ ID NO 8
<211> LENGTH: 117
<212> TYPE: PRT
<213> ORGANISM: Artificial Sequence
<220> FEATURE:
<223> OTHER INFORMATION: Murine derived antibody sequence

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Met
            35                  40                  45
```

Gly Arg Ile Tyr Pro Gly Asp Gly Asn Thr His Tyr Ala Gln Lys Phe
            50                  55                  60

Gln Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Gly Glu Gly Tyr Leu Asp Pro Met Asp Tyr Trp Gly Gln Gly Thr Leu
            100                 105                 110

Val Thr Val Ser Ser
            115

<210> SEQ ID NO 9
<211> LENGTH: 117
<212> TYPE: PRT
<213> ORGANISM: Artificial Sequence
<220> FEATURE:
<223> OTHER INFORMATION: Murine derived antibody sequence

<400> SEQUENCE: 9

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Thr Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asn Thr His Tyr Ala Gln Lys Phe
            50                  55                  60

Gln Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Gly Glu Gly Tyr Leu Asp Pro Met Asp Tyr Trp Gly Gln Gly Thr Leu
            100                 105                 110

Val Thr Val Ser Ser
            115

<210> SEQ ID NO 10
<211> LENGTH: 117
<212> TYPE: PRT
<213> ORGANISM: Artificial Sequence
<220> FEATURE:
<223> OTHER INFORMATION: Murine derived antibody sequence

<400> SEQUENCE: 10

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Ser
                20                  25                  30

Trp Met Asn Trp Val Arg Gln Ala Pro Gly Lys Gly Leu Glu Trp Met
            35                  40                  45

Gly Arg Ile Tyr Pro Gly Asp Gly Gln Thr His Tyr Ala Gln Lys Phe
            50                  55                  60

Gln Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Gly Glu Gly Tyr Leu Asp Pro Met Asp Tyr Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Murine derived antibody sequence

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Lys Gly Leu Glu Trp Met
        35                  40                  45

Gly Arg Ile Tyr Pro Gly Asp Gly Gln Thr His Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Glu Gly Tyr Leu Asp Pro Met Asp Tyr Trp Gly Gln Gly Thr Leu
            100                 105                 110

Val Thr Val Ser Ser
        115

<210> SEQ ID NO 12
<211> LENGTH: 11
<212> TYPE: PRT
<213> ORGANISM: Artificial Sequence
<220> FEATURE:
<223> OTHER INFORMATION: Murine derived antibody sequence

<400> SEQUENCE: 12

Ser Ala Ser Gln Gly Ile Asn Asn Tyr Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Murine derived antibody sequence

<400> SEQUENCE: 13

Tyr Thr Ser Gly Leu His Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Murine derived antibody sequence

<400> SEQUENCE: 14

Gln Gln Tyr Ser Ile Leu Pro Trp Thr
1               5

<210> SEQ ID NO 15

```
<211> LENGTH: 108
<212> TYPE: PRT
<213> ORGANISM: Artificial Sequence
<220> FEATURE:
<223> OTHER INFORMATION: Murine derived antibody sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

His Tyr Thr Ser Gly Leu His Ala Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg
            100                 105

<210> SEQ ID NO 16
<211> LENGTH: 108
<212> TYPE: PRT
<213> ORGANISM: Artificial Sequence
<220> FEATURE:
<223> OTHER INFORMATION: Murine derived antibody sequence

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

His Tyr Thr Ser Gly Leu His Ala Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg
            100                 105

<210> SEQ ID NO 17
<211> LENGTH: 108
<212> TYPE: PRT
<213> ORGANISM: Artificial Sequence
<220> FEATURE:
<223> OTHER INFORMATION: Murine derived antibody sequence

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45
```

```
His Tyr Thr Ser Gly Leu His Ala Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg
            100                 105
```

<210> SEQ ID NO 18
<211> LENGTH: 106
<212> TYPE: PRT
<213> ORGANISM: Artificial Sequence
<220> FEATURE:
<223> OTHER INFORMATION: Murine derived antibody sequence

<400> SEQUENCE: 18

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 19
<211> LENGTH: 330
<212> TYPE: PRT
<213> ORGANISM: Artificial Sequence
<220> FEATURE:
<223> OTHER INFORMATION: Murine derived antibody sequence

<400> SEQUENCE: 19

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140
```

-continued

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

ANTI HUMAN INTERLEUKIN-1 RECEPTOR ACCESSORY PROTEIN (IL1 RAP) ANTIBODIES AND USES THEREOF

CROSS REFERENCE TO RELATED APPLICATIONS

This application is a continuation of U.S. application Ser. No. 15/707,593, filed Sep. 18, 2017, which is a divisional of U.S. application Ser. No. 15/255,585, filed Sep. 2, 2016, now U.S. Pat. No. 9,796,783, which is continuation application of International Application No. PCT/GB2015/050647, which was filed on Mar. 5, 2015, and claims priority to United Kingdom Application No. GB 1403875.6, which was filed on Mar. 5, 2014, all of which are incorporated by reference in their entirety.

FIELD OF INVENTION

The present invention relates to antibody-based agents for the treatment and diagnosis of diseases and conditions associated with a IL-1 biomarker (specifically, IL1RAP) and/or responsive to inhibition of IL-1 signalling. In particular, there are provided antibody-based agents for the treatment and diagnosis of cancers, including but not limited to chronic myeloid leukemia (CML), acute myeloid leukemia (AML) and cancers associated with solid tumour formation (such as melanoma, lung cancer, and cancer of the breast).

BACKGROUND

Interleukin-1 Biology

Interleukin-1 (IL-1) is a potent pro-inflammatory cytokine that can be produced by a variety of cell types, including mononuclear phagocytes, in response to infection and inflammation. The IL-1 family consists of seven agonists, including IL-1α and IL-1β, and three naturally occurring receptor antagonists, including the IL-1 receptor antagonist (IL-1Ra) (Dinarello, C A, Blood 1996, 87(6): 2095-147). Two IL-1 receptors, IL-1R type I and IL-1R type II, have been identified. Both receptors can interact with all three forms of the IL-1 family molecules. IL-1RI is responsible for mediating IL-1-induced cellular activation. However, the IL-1/IL-1RI complex cannot signal by itself, but is dependent on association with a second receptor chain, IL-1R Accessory Protein (IL1RAP) (Dinarello, C A, Blood 1996, 87(6): 2095-147). In contrast to IL-1RI, IL-1RII does not induce cellular activation upon binding to IL-1 and thus IL-1RII functions as regulatory decoy receptor, leading to a net decrease in IL-1 available to bind to IL-1RI.

In addition to IL1-signaling, IL1RAP is critical for mediating the effects of IL33, through the ST2/IL1RAP complex, and IL36, through the IL1Rrp2/IL1RAP complex (Garlanda et al, Immunity. 2013 Dec. 12; 39(6):1003-18)

IL-1 is a potent pro-inflammatory cytokine, which is induced at sites of local infection or inflammation and is involved in the regulation of a variety of physiological and cellular events (summarised in Dinarello C A, CHEST, 2000, 118: 503-508 and Dinarello, C A, Clin Exp Rheumatol, 2002, 20(5 Suppl 27): S1-13). It is capable of activating several cell types including leukocytes and endothelial cells. IL-1 induces and amplifies immunological responses by promoting the production and expression of adhesion molecules, cytokines, chemokines and other inflammatory mediators such as prostaglandin $E_2$ and nitric oxide (NO). As a consequence, local inflammation is amplified and sustained. In addition, the IL-1-induced production of inflammatory mediators results in fever, headache, hypotension and weight loss. Furthermore, IL-1 is a hematopoietic growth factor and has been shown to reduce the nadir of leukocytes and platelets in patients during bone marrow transplantation. IL-1 has also been shown to promote angiogenesis by inducing the production of vascular endothelial growth factor, thereby promoting pannus formation and blood supply in rheumatic joints. Finally, IL-1 has been shown to promote the bone and cartilage degradation in rheumatic diseases.

The Role of IL-1 in Disease

IL-1 is implicated in a wide range of diseases and conditions ranging from gout to cancer (for reviews, see Dinarello et al., 2012, Nature Reviews 11:633-652 and Dinarello, 2014, Mol. Med. 20(suppl. 1):S43-S58; the disclosures of which are incorporated herein by reference), including:

Joint, bone and muscle diseases, such as rheumatoid arthritis and osteoarthritis;

Hereditary systemic autoinflammatory diseases, such as familial Mediterranean fever;

Systemic autoinflammatory diseases, such as systemic juvenile idiopathic arthritis and adult-onset Still's disease;

Common inflammatory diseases, such as gout and type 2 diabetes;

Acute-onset ischemic diseases, such as myocardial infarction; and

Cancer.

A number of therapies for blocking IL-1 activity are approved and in development. Targeting IL-1 began in 1993 with the introduction of anakinra (Kineret; Amgen), a recombinant form of the naturally occurring IL-1 receptor antagonist (IL-1Ra), which blocks the activity of both IL-1α and IL-1β; this therapeutic has since been used to demonstrate a role for IL-1 in numerous diseases (see above). Anakinra currently dominates the field of IL-1 therapeutics owing to its good safety record, short half-life and multiple routes of administration. Neutralising IL-1 with antibodies or soluble receptors has also proved to be effective, and the soluble decoy receptor rilonacept (Arcalyst; Regeneron) and the anti-IL-13 neutralizing monoclonal antibody canakinumab (Ilaris; Novartis) have now been approved. Other therapeutic approaches, including IL-1α neutralisation, a therapeutic vaccine targeting IL-13 and a chimeric IL-1Ra, are in early clinical trials. In addition, orally active small-molecule inhibitors of IL-1 production, such as caspase 1 inhibitors, have been developed and are being tested IL1RAP as a Biomarker for Neoplastic Disorders Tumour biomarkers are endogenous proteins or metabolites whose amounts or modifications are indicative of tumour state, progression characteristics, and response to therapies. They are present in tumour tissues or body fluids and encompass a wide variety of molecules, including transcription factors, cell surface receptors, and secreted proteins. Effective tumour markers are in great demand since they have the potential to reduce cancer mortality rates by facilitating diagnosis of cancers at early stages and by helping to individualize treatments. During the last decade, improved understanding of carcinogenesis and tumour progression has revealed a large number of potential tumour markers. It is predicted that even more will be discovered in the near future with the application of current technologies such as tissue microarrays, antibody arrays, and mass spectrometry.

Interleukin-1 receptor accessory protein (IL1RAP) has previously been identified as cell-surface biomarker associated with haematological neoplastic disorders such as chronic myeloid leukemia (CML), acute myeloid leukemia (AML) and myelodysplatic syndromes (MDS) (for example, see WO 2011/021014 to Cantargia A B, Järås et al., 2010, *Proc Natl Acad Sci USA* 107(37):16280-5, Askmyr et al., 2013, *Blood.* 121(18):3709-13 and Barreyro et al., 2012, *Blood* 120(6):1290-8, the disclosures of which are incorporated herein by reference). More recently, the usefulness of IL1RAP as a diagnostic and therapeutic biomarker for solid tumours, such as melanomas, has also been revealed (see WO 2012/098407 to Cantargia AB, the disclosures of which are incorporated herein by reference).

The present invention thus seeks to provide improved antibodies for use in the diagnosis and treatment of diseases and conditions associated with the IL1RAP biomarker and/or responsive to inhibition of IL-1 and/or IL-33 signalling

SUMMARY OF INVENTION

A first aspect of the invention provides an antibody or an antigen-binding fragment thereof ('antibody polypeptides') with binding specificity for interleukin-1 receptor accessory protein ('IL1RAP'), wherein the antibody or antigen-binding fragment is capable of inhibiting the binding of reference antibody 'CAN04' to human IL1RAP.

By "interleukin-1 receptor accessory protein", "IL1RAP" and "IL1-RAP" we specifically include the human IL1RAP protein, for example as described in GenBank Accession No. AAB84059, NCBI Reference Sequence: NP_002173.1 and UniProtKB/Swiss-Prot Accession No. Q9NPH3-1 (see also Huang et al., 1997, *Proc. Natl. Acad. Sci. USA.* 94 (24), 12829-12832, the disclosures of which are incorporated herein by reference). IL1RAP is also known in the scientific literature as IL1R3, C3orf13, FLJ37788, IL-1RAcP and EG3556.

Thus, the antibody polypeptides of the invention have specificity for IL1RAP. By "specificity" we mean that the antibody polypeptide is capable of binding to IL1RAP in vivo, i.e. under the physiological conditions in which IL1RAP exists within the human body. Preferably, the antibody polypeptide does not bind to any other protein in vivo. Such binding specificity may be determined by methods well known in the art, such as ELISA, immunohistochemistry, immunoprecipitation, Western blots and flow cytometry using transfected cells expressing IL1RAP. Advantageously, the antibody polypeptide is capable of binding selectively to IL1RAP, i.e. it binds at least 10-fold more strongly to IL1RAP than to any other proteins.

By "reference antibody 'CAN04'" we include an intact IgG antibody comprising heavy and light chain variable regions having the amino acid sequences of SEQ ID NOS: 1 and 2, respectively. Unless otherwise stated, references herein to "CAN04" refer to an intact IgG antibody comprising (a) a heavy chain comprising a variable region as defined by SEQ ID NO:1 and a constant region as defined by SEQ ID NO: 19, and (b) a light chain comprising a variable region as defined by SEQ ID NO:2 and a constant region as defined by SEQ ID NO: 18. Alternatively, a humanised version of CAN04 ('hCAN04') may be used as the reference antibody. For example, the reference antibody may be an intact IgG antibody comprising (a) a heavy chain comprising a variable region as defined by any one of SEQ ID NOS:8 to 11 and a constant region as defined by SEQ ID NO: 19, and (b) a light chain comprising a variable region as defined by any one of SEQ ID NOS:15 to 17 and a constant region as defined by SEQ ID NO: 18.

As discussed below, the reference antibody 'CAN04' binds to domain 2 of IL1RAP. Thus, it will be appreciated that the antibody or an antigen-binding fragment of the invention also binds to domain 2 of IL1RAP By "capable of inhibiting the binding of reference antibody 'CAN04' to human IL1RAP" we mean that the presence of the antibody polypeptides of the invention inhibits, in whole or in part, the binding of 'CAN04' to human IL1RAP. Such competitive binding inhibition can be determined using assays and methods well known in the art, for example using BIAcore chips with immobilised IL1RAP and incubating with the reference antibody 'CAN04' with and without an antibody polypeptide to be tested. Alternatively, a pair-wise mapping approach can be used, in which the reference antibody 'CAN04' is immobilised to the surface of the BIAcore chip, IL1RAP antigen is bound to the immobilised antibody, and then a second antibody is tested for simultaneous IL1RAP-binding ability (see 'BIAcore Assay Handbook', GE Healthcare Life Sciences, 29-0194-00 AA 05/2012; the disclosures of which are incorporated herein by reference).

In a further alternative, competitive binding inhibition can be determined using flow cytometry. For example, to test whether a test antibody is able to inhibit the binding of the CAN04 reference antibody to a cell surface antigen, cells expressing the antigen can be pre-incubated with the test antibody for 20 min before cells are washed and incubated with the reference CAN04 antibody conjugated to a fluorophore, which can be detected by flow cytometry. If the pre-incubation with the test antibody reduces the detection of the reference CAN04 antibody in flow cytometry, the test antibody inhibits the binding of the reference antibody to the cell surface antigen. If the antibody to be tested exhibits high affinity for IL1RAP, then a reduced pre-incubation period may be used (or even no pre-incubation at all).

In a further alternative, competitive binding inhibition can be determined using an ELISA (e.g. as described in Example J).

By "an antibody or an antigen-binding fragment thereof" we include substantially intact antibody molecules, as well as chimaeric antibodies, humanised antibodies, isolated human antibodies, single chain antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include, but are not necessarily limited to, Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

The phrase "an antibody or an antigen-binding fragment thereof" is also intended to encompass antibody mimics (for example, non-antibody scaffold structures that have a high degree of stability yet allow variability to be introduced at certain positions). Those skilled in the art of biochemistry will be familiar with many such molecules, as discussed in Gebauer & Skerra, 2009, *Curr Opin Chem Biol* 13(3): 245-255 (the disclosures of which are incorporated herein by reference). Exemplary antibody mimics include: affibodies (also called Trinectins; Nygren, 2008, *FEBS J*, 275, 2668-2676); CTLDs (also called Tetranectins; *Innovations Pharmac. Technol*. (2006), 27-30); adnectins (also called monobodies; *Meth. Mol. Biol.*, 352 (2007), 95-109); anticalins (*Drug Discovery Today* (2005), 10, 23-33); DARPins (ankyrins; *Nat. Biotechnol*. (2004), 22, 575-582); avimers (*Nat. Biotechnol*. (2005), 23, 1556-1561); microbodies (*FEBS J*, (2007), 274, 86-95); peptide aptamers (*Expert. Opin. Biol. Ther*. (2005), 5, 783-797); Kunitz domains (*J. Pharmacol. Exp. Ther*. (2006) 318, 803-809); affilins (*Trends. Biotechnol*. (2005), 23, 514-522); affimers (Avacta Life Sciences, Wetherby, UK).

Also included within the scope of the invention are chimeric T-cell receptors (also known as chimeric T cell receptors, chimeric immunoreceptors, and chimeric antigen receptors or CARs) (see Pule et al., 2003, *Cytotherapy* 5(3):211-26, the disclosures of which are incorporated herein by reference). These are engineered receptors, which graft an arbitrary specificity onto an immune effector cell. Typically, CARs are used to graft the specificity of a monoclonal antibody onto a T cell; with transfer of their coding sequence facilitated by retroviral vectors. The most common form of such molecules is fusions comprising a single-chain variable fragment (scFv) derived from a monoclonal antibody fused to CD3-zeta transmembrane and endodomain. When T cells express this fusion molecule, they recognize and kill target cells that express the transferred monoclonal antibody specificity.

Persons skilled in the art will further appreciate that the invention also encompasses modified versions of antibodies induction of in vivo production of antibody molecules, screening of immunoglobulin libraries (Orlandi. et al, 1989. *Proc. Natl. Acad. Sci. U.S.A.* 86:3833-3837; Winter et al., 1991, Nature 349:293-299, the disclosures of which are incorporated herein by reference) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120, the disclosures of which are incorporated herein by reference).

Suitable methods for the production of monoclonal antibodies are also disclosed in "*Monoclonal Antibodies: A manual of techniques*", H Zola (CRC Press, 1988, the disclosures of which are incorporated herein by reference) and in "*Monoclonal Hybridoma Antibodies: Techniques and Applications*", J G R Hurrell (CRC Press, 1982, the disclosures of which are incorporated herein by reference).

Likewise, antibody fragments can be obtained using methods well known in the art (see, for example, Harlow & Lane, 1988, *"Antibodies: A Laboratory Manual"*, Cold Spring Harbor Laboratory, New York, the disclosures of which are incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

The antibodies of the invention are defined by reference to the variable regions of a murine-derived antibody, designated 'CAN04', which comprises:

(a) a heavy chain variable region having the amino acid sequence of SEQ ID NO: 1:

[SEQ ID NO: 1]

Q V Q L Q Q S G P E L L K P G A S V K I S C K A S G

Y A F S S S W M N W V K Q R P G K G L E W I G R I

Y P G D G N T H Y S G K F K G K A T L T A D K S S

S I A Y M Q L S S L T S E D S A V Y F C G E G Y L D

P M D Y W G Q G T S V T V S S
and (b) a light chain variable region having the amino acid sequence of SEQ ID NO: 2:

[SEQ ID NO: 2]

D I Q M T Q T T S S L S A S L G D R V T I S C S A S

Q G I N N Y L N W Y Q Q K P D G T V K L L I H Y T S

G L H A G V P S R F S G S G S G T D Y S L T I S N L

E P E D V A T Y Y C Q Q Y S I L P W T F G G G T K

L E I K R and antigen-binding fragments thereof, whether existing now or in the future, e.g. modified by the covalent attachment of polyethylene glycol or another suitable polymer (see below).

Methods of generating antibodies and antibody fragments are well known in the art. For example, antibodies may be generated via any one of several methods which employ The term "amino acid" as used herein includes the standard twenty genetically-encoded amino acids and their corresponding stereoisomers in the 'D' form (as compared to the natural 'L' form), omega-amino acids and other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the antibody polypeptides as defined herein comprise or consist of L-amino acids.

It will be appreciated by persons skilled in the art that any intact IgG antibody comprising the above variable regions may be used as the reference antibody to identify antibody polypeptides of the invention that competitively inhibit CAN04 binding to IL1RAP.

Thus, in one embodiment, the CAN04 antibody used as a reference to determined competitive binder is an intact IgG antibody comprising:
  (a) a heavy chain comprising a variable domain of SEQ ID NO:1 grafted on to a murine IgG1 or IgG2a constant region
  (b) a light chain comprising a variable domain of SEQ ID NO:2 grafted on to a murine kappa constant region.

Alternatively, the reference antibody may be a chimeric, intact IgG antibody comprising:
  (a) a heavy chain comprising a variable domain of SEQ ID NO:1 grafted on to an human IgG1 constant region (for example, as encoded by the pFUSEss-CHIg-hG1 vector InvivoGen, San Diego, USA)
  (b) a light chain comprising a variable domain of SEQ ID NO:2 grafted on to a human kappa constant region (for example, as encoded by the pFUSE2ss-CLIg-hk vector InvivoGen, San Diego, USA).

Competitive binding typically arises because the test antibody binds at, or at least very close to, the epitope on the antigen to which binds the reference antibody (in this case, CAN04). However, it will be appreciated by persons skilled in the art that competitive binding may also arise by virtue of steric interference; thus, the test antibody may bind at an epitope different from that to which the reference antibody binds but may still be of sufficient size or configuration to hinder the binding of the reference antibody to the antigen.

The antibodies and antigen-binding fragments of the present invention were identified after extensive screening of a large number of anti-IL1RAP antibodies, on the basis of exhibiting properties that make them particularly suitable as diagnostic and therapeutic agents for cancer.

Thus, in one embodiment, the antibody or antigen-binding fragment exhibits one or more of the following properties:
  (a) a binding affinity ($K_D$) for human IL1RAP of 200 pM or greater, i.e. the $K_D$<200 pM (for example, as determined in Example A);
  (b) cross-reactivity with IL1RAP from *Macaca fascicularis* (for example, as determined in Example D);
  (c) an inhibitory action on IL1 signalling (IL-1α and/or IL-1β; for example, as determined in Example E);
  (d) capability of inducing antibody-dependent cell-mediated cytotoxicity (ADCC) in one or more cancer cell lines (such as a CML, ALL and/or melanoma cell lines) (for example, as determined in Example F); and/or
  (e) capability of internalisation upon binding to one or more cancer cell lines (such as a CML, AML and/or melanoma cell line) (for example, as determined in Example G).

Advantageously, the antibody or antigen-binding fragment exhibits all of the above properties.

In an alternative embodiment, the antibody or antigen-binding fragment exhibits one or more of properties (a), (b), (c) and (e) above, but is not capable of inducing ADCC.

In one embodiment, the antibody or antigen-binding fragment is capable of binding to an epitope on the extracellular domain of IL1RAP which overlaps, at least in part, with the epitope on IL1RAP to which reference antibody CAN04 is capable of binding. Thus, the antibody or antigen-binding fragment may be capable of binding to an epitope located at/within domain 2 of IL1RAP (see Wang et al., 2010, *Nature Immunology*, 11:905-912, the disclosures of which are incorporated herein by reference), i.e. within amino acids 135 to 234 of IL1RAP (see Accession No. Q9NPH3 within UniProtKB/Swiss-Prot). For example, the epitope to which the antibody or antigen-binding fragment may be located within amino acids 135 to 154, 155 to 174, 175 to 194, 195 to 214 or between amino acids 215 to 234 of IL1RAP. However, it will be appreciated that the epitope may be non-linear.

In one embodiment, the antibody polypeptide of the invention comprises or consists of an intact antibody (such as an IgG1 antibody).

In an alternative embodiment, the antibody polypeptide of the invention comprises or consists of an antigen-binding fragment selected from the group consisting of Fv fragments (e.g. single chain Fv and disulphide-bonded Fv), Fab-like fragments (e.g. Fab fragments, Fab' fragments and F(ab)$_2$ fragments) and domain antibodies (e.g. single $V_H$ variable domains or $V_L$ variable domains).

In a further embodiment, as discussed above, the polypeptide of the invention comprises or consists of an antibody mimic selected from the group comprising or consisting of affibodies, tetranectins (CTLDs), adnectins (monobodies), anticalins, DARPins (ankyrins), avimers, iMabs, microbodies, peptide aptamers, Kunitz domains and affilins.

In a preferred embodiment, the antibody or antigen-binding fragment thereof according to the first aspect of the invention comprises a heavy chain variable region comprising the following CDRs:
  a) GYAFSSS [SEQ ID NO: 3] or an amino acid sequence having at least 60% sequence identity therewith, for example at least 70%, 80%, or 90% sequence identity;
  b) YPGDGN [SEQ ID NO: 4] or an amino acid sequence having at least 60% sequence identity therewith, for example at least 70%, 80%, or 90% sequence identity; and/or
  c) GYLDPMDY [SEQ ID NO: 5] or an amino acid sequence having at least 60% sequence identity therewith, for example at least 70%, 80%, or 90% sequence identity.

Thus, the antibody or antigen-binding fragment thereof may comprise a heavy chain variable region comprising the CDRs of SEQ ID NOs 3, 4 and 5.

For example, the antibody or antigen-binding fragment thereof may comprise a heavy chain variable region having the amino acid sequence of the corresponding region of the CAN04 reference antibody, i.e. SEQ ID NO:1.

However, it will be appreciated that a low level of mutation (typically, just one or two amino acids) within a CDR sequence may be tolerated without loss of the specificity of the antibody or antigen-binding fragment for IL1RAP.

Percent identity can be determined by, for example, the LALIGN program (Huang and Miller, *Adv. Appl. Math.* (1991) 12:337-357, the disclosures of which are incorporated herein by reference) at the Expasy facility site (http://www.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (as described in Thompson et al., 1994, *Nucl. Acid Res.* 22:4673-4680, which is incorporated herein by reference). The parameters used may be as follows:

Fast pair-wise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

In a further preferred embodiment, the antibody or antigen-binding fragment thereof according to the first aspect of the invention comprises a heavy chain variable region comprising the following CDRs:

a) GYAFSSSWMN [SEQ ID NO: 6] or an amino acid sequence having at least 60% sequence identity therewith, for example at least 70%, 80%, or 90% sequence identity;

b) RIYPGDGNTHYSGKFKG [SEQ ID NO: 7] or an amino acid sequence having at least 60% sequence identity therewith, for example at least 70%, 80%, or 90% sequence identity; and c) GYLDPMDY [SEQ ID NO: 5] or an amino acid sequence having at least 60% sequence identity therewith, for example at least 70%, 80%, or 90% sequence identity.

For example, the antibody polypeptide may comprise a heavy chain variable region comprising the CDRs of SEQ ID NOs 6, 7 and 5.

As indicated above, the CAN04 reference antibody is a murine antibody. However, the component heavy and light chains of this antibody may be humanised in order to produce antibody polypeptides more suitable for use in humans, e.g. due to their reduced immunogenicity. For example, the CDRs of SEQ ID NOs 3, 4 and 5 (or the CDRs of SEQ ID NOs 6, 7 and 5) may be engrafted into a human variable region framework.

It will be appreciated by persons skilled in the art that for human therapy, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596, the disclosures of which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567, the disclosures of which are incorporated herein by reference) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95, the disclosures of which are incorporated herein by reference).

Thus, the antibody or antigen-binding fragment thereof of the invention may be humanised, for example it may comprise a heavy chain variable region having one of the following amino acid sequence of any one of SEQ ID NOs: 8 to 11 or an amino acid sequence having at least 90% sequence identity therewith:

a)
[SEQ ID NO: 8]
Q V Q L V Q S G A E V K K P G S S V K V S C K A

S G Y A F S S S W M N W V R Q A P G Q G L E W

M G R I Y P G D G N T H Y A Q K F Q G R V T L T

A D K S T S T A Y M E L S S L R S E D T A V Y Y

C G E G Y L D P M D Y W G Q G T L V T V S S;

b)
[SEQ ID NO: 9]
Q V Q L V Q S G A E V K K P G S S V K V S C K A

S G Y A F T S S W M N W V R Q A P G Q G L E W

M G R I Y P G D G N T H Y A Q K F Q G R V T L T

-continued

ADKSTSTAYMELSSLRSEDTAVYYC

GEGYLDPMDYWGQGTLVTVSS;

c)
[SEQ ID NO: 10]
QVQLVQSGAEVKKPGSSVKVSCKA

SGYTFTSSWMNWVRQAPGKGLEWM

GRIYPGDGQTHYAQKFQGRVTLTA

DKSTSTAYMELSSLRSEDTAVYYC

GEGYLDPMDYWGQGTLVTVSS;
or d)
[SEQ ID NO: 11]
QVQLVQSGAEVKKPGSSVKVSCKA

SGYTFTSSWMNWVRQAPGKGLEWM

GRIYPGDGQTHYAQKFQGRVTITA

DKSTSTAYMELSSLRSEDTAVYYC

GEGYLDPMDYWGQGTLVTVSS.

For example, the antibody or antigen-binding fragment thereof may comprise a heavy chain variable region having an amino acid sequence of any one of SEQ ID NOs: 8 to 11.

In a related preferred embodiment, the antibody or antigen-binding fragment thereof comprises a light chain variable region comprising the following CDRs:

a) SASQGINNYLN [SEQ ID NO: 12] or an amino acid sequence having at least 60% sequence identity therewith, for example at least 70%, 80%, or 90% sequence identity;

b) YTSGLHA [SEQ ID NO: 13] or an amino acid sequence having at least 60% sequence identity therewith, for example at least 70%, 80%, or 90% sequence identity; and/or c) QQYSILPWT [SEQ ID NO: 14] or an amino acid sequence having at least 60% sequence identity therewith, for example at least 70%, 80%, or 90% sequence identity.

Thus, the antibody or antigen-binding fragment thereof may comprise a light chain variable region comprising the CDRs of SEQ ID NOs 12, 13 and 14.

For example, the antibody or antigen-binding fragment thereof may comprise a light chain variable region having the amino acid sequence of the corresponding region of the murine CAN04 reference antibody, i.e. SEQ ID NO:2.

As in the case of the heavy chain variable region detailed above, it will be appreciated that the light chain variable region of the antibody polypeptide of the invention may be humanised in order to produce agents more suitable for use in humans. For example, the CDRs of SEQ ID NOs 12, 13 and 14 may be engrafted into a human variable region framework.

Thus, the antibody or antigen-binding fragment thereof may comprise a light chain variable region which comprises or consists of the amino acid sequence of any one of SEQ ID NOs: 15 to 17 or an amino acid sequence having at least 90% sequence identity therewith:

a)
[SEQ ID NO: 15]
DIQMTQSPSSLSASVGDRVTITCSA

SQGINNYLNWYQQKPGKAPKLLIHY

TSGLHAGVPSRFSGSGSGTDYTLTI

SSLQPEDVATYYCQQYSILPWTFG

GGTKVEIKR;

b)
[SEQ ID NO: 16]
DIQMTQSPSSLSASVGDRVTITCQA

SQGINNYLNWYQQKPGKAPKLLIHY

TSGLHAGVPSRFSGSGSGTDYTLTI

SSLEPEDVATYYCQQYSILPWTFG

GGTKVEIKR;
or c)
[SEQ ID NO: 17]
DIQMTQSPSSLSASVGDRVTITCQA

SQGINNYLNWYQQKPGKAPKLLIHY

TSGLHAGVPSRFSGSGSGTDFTLTI

SSLEPEDVATYYCQQYSILPWTFG

GGTKVEIKR.

For example, the antibody or antigen-binding fragment thereof may comprise a light chain variable region having an amino acid sequence of any one of SEQ ID NOs: 15 to 17.

In one embodiment, the antibody or antigen-binding fragment thereof comprises a murine heavy chain variable region which comprises or consists of the amino acid sequence of any one of SEQ ID NO: 1 and a murine light chain variable region which comprises or consists of the amino acid sequence of any one of SEQ ID NO: 2.

Alternatively, the antibody or antigen-binding fragment thereof may comprise a humanised heavy chain variable region which comprises or consists of the amino acid sequence of any one of SEQ ID NOs: 8 to 11 and a humanised light chain variable region which comprises or consists of the amino acid sequence of any one of SEQ ID NOs: 15 to 17.

For example, the antibody or antigen-binding fragment thereof may comprise:

a) a heavy chain variable region which comprises or consists of the amino acid sequence of SEQ ID NO: 8 and a light chain variable region which comprises or consists of the amino acid sequence of SEQ ID NO: 15;

b) a heavy chain variable region which comprises or consists of the amino acid sequence of SEQ ID NO: 9 and a light chain variable region which comprises or consists of the amino acid sequence of SEQ ID NO: 15;

c) a heavy chain variable region which comprises or consists of the amino acid sequence of SEQ ID NO: 10 and a light chain variable region which comprises or consists of the amino acid sequence of SEQ ID NO: 15;

d) a heavy chain variable region which comprises or consists of the amino acid sequence of SEQ ID NO: 11 and a light chain variable region which comprises or consists of the amino acid sequence of SEQ ID NO: 15;

e) a heavy chain variable region which comprises or consists of the amino acid sequence of SEQ ID NO: 8 and a light chain variable region which comprises or consists of the amino acid sequence of SEQ ID NO: 16;

f) a heavy chain variable region which comprises or consists of the amino acid sequence of SEQ ID NO: 9 and a light chain variable region which comprises or consists of the amino acid sequence of SEQ ID NO: 16;

g) a heavy chain variable region which comprises or consists of the amino acid sequence of SEQ ID NO: 10 and a light chain variable region which comprises or consists of the amino acid sequence of SEQ ID NO: 16;

h) a heavy chain variable region which comprises or consists of the amino acid sequence of SEQ ID NO: 11 and a light chain variable region which comprises or consists of the amino acid sequence of SEQ ID NO: 16;

i) a heavy chain variable region which comprises or consists of the amino acid sequence of SEQ ID NO: 8 and a light chain variable region which comprises or consists of the amino acid sequence of SEQ ID NO: 17;

j) a heavy chain variable region which comprises or consists of the amino acid sequence of SEQ ID NO: 9 and a light chain variable region which comprises or consists of the amino acid sequence of SEQ ID NO: 17;

k) a heavy chain variable region which comprises or consists of the amino acid sequence of SEQ ID NO: 10 and a light chain variable region which comprises or consists of the amino acid sequence of SEQ ID NO: 17; or l) a heavy chain variable region which comprises or consists of the amino acid sequence of SEQ ID NO: 11 and a light chain variable region which comprises or consists of the amino acid sequence of SEQ ID NO: 17.

It will be appreciated by persons skilled in the art that the above-defined humanised antibodies or antigen-binding fragments of the invention may further comprise a heavy chain constant region, or part thereof (see below).

In one embodiment, the antibody polypeptide comprises a CH1, CH2 and/or CH3 region of an IgG heavy chain (such as an IgG1, IgG2, IgG3 or IgG4 heavy chain). Thus, the antibody polypeptide may comprise part or all of the constant regions from an IgG1 heavy chain. For example, the antibody polypeptide may be a Fab fragment comprising CH1 and CL constant regions, combined with any of the above-defined heavy and light variable regions respectively.

Likewise, the above-defined antibodies or antigen-binding fragments of the invention may further comprise a light chain constant region, or part thereof (see below). For example, the antibody polypeptide may comprise a CL region from a kappa or lambda light chain.

For example, the antibody polypeptide may comprise the following constant regions:

```
(a) Ig kappa chain C region (Homo sapiens) (UnitProt Accession
No. P01834)
                                                   [SEQ ID NO: 18]
TVAAPSVFIF PPSDEQLKSG TASVVCLLNN FYPREAKVQW KVDNALQSGN

SQESVTEQDS KDSTYSLSST LTLSKADYEK HKVYACEVTH QGLSSPVTKS

FNRGEC (b) Ig gamma-1 chain C region (Homo sapiens) (UnitProt Accession
No. P01857)
                                                   [SEQ ID NO: 19]
ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCP PCPAPELLGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSREE MTKNQVSLTC

LVKGFYPSDI AVEWESNGQP ENNYKTTPPV LDSDGSFFLY SKLTVDKSRW

QQGNVFSCSV MHEALHNHYT QKSLSLSPGK
```

In an alternative embodiment, naturally occurring variants of the above constant regions may be utilised (e.g. see Jefferis & Lefranc, 2009, *MAbs* 1(4):332-8, the disclosures of which are incorporated herein by reference). For example, the light china constant region may comprise or consist of SEQ ID NO: 18 having a W40R and/or V83L mutation and/or the heavy china constant region may comprise or consist of SEQ ID NO: 19 having a K97R, D239E and/or L241M mutation, or without the C-terminal lysine/K (wherein the position of the amino acid mutations is defined using the Eu Numbering Scheme, which differs from the numbering in SEQ ID NOS: 18 and 19; see Edelman et al., 1969, *Proc. Natl. Acad. Sci. USA*, 63:78-85, the disclosures of which are incorporated herein by reference).

Thus, exemplary antibody polypeptides of the invention comprise:
(a) a heavy chain comprising a variable region of SEQ ID NO: 1, 8, 9, 10 or 11 together with a constant region of SEQ ID NO: 19; and
(b) a light chain comprising a variable region of SEQ ID NO: 2, 15, 16 or 17 together with a constant region of SEQ ID NO: 18.

In a related embodiment, the antibody polypeptide may comprise an antibody Fc-region (e.g. the CH2 and CH3 regions of an IgG heavy chain). It will be appreciated by a skilled person that the Fc portion may be from an IgG antibody, or from a different class of antibody (such as IgM, IgA, IgD or IgE). In one embodiment, the Fc region is from an IgG1, IgG2, IgG3 or IgG4 antibody.

The Fc region may be naturally-occurring (e.g. part of an endogenously produced antibody) or may be artificial (e.g. comprising one or more point mutations relative to a naturally-occurring Fc region).

As is well documented in the art, the Fc region of an antibody mediates its serum half-life and effector functions, such as complement-dependent cytotoxicity (CDC), antibody-dependent cellular cytotoxicity (ADCC) and antibody-dependent cell phagocytosis (ADCP).

Engineering the Fc region of a therapeutic monoclonal antibody or Fc fusion protein allows the generation of molecules that are better suited to the pharmacology activity required of them (Strohl, 2009, *Curr Opin Biotechnol* 20(6): 685-91, the disclosures of which are incorporated herein by reference).

(a) Engineered Fc Regions for Increased Half-Life

One approach to improve the efficacy of a therapeutic antibody is to increase its serum persistence, thereby allowing higher circulating levels, less frequent administration and reduced doses.

The half-life of an IgG depends on its pH-dependent binding to the neonatal receptor FcRn. FcRn, which is expressed on the surface of endothelial cells, binds the IgG in a pH-dependent manner and protects it from degradation.

Some antibodies that selectively bind the FcRn at pH 6.0, but not pH 7.4, exhibit a higher half-life in a variety of animal models.

Several mutations located at the interface between the CH2 and CH3 domains, such as T250Q/M428L (Hinton et al., 2004, *J Biol Chem.* 279(8):6213-6, the disclosures of which are incorporated herein by reference) and M252Y/S254T/T256E+H433K/N434F (Vaccaro et al., 2005, *Nat. Biotechnol.* 23(10):1283-8, the disclosures of which are incorporated herein by reference), have been shown to increase the binding affinity to FcRn and the half-life of IgG1 in vivo.

(b) Engineered Fc Regions for Altered Effector Function

Depending on the therapeutic antibody or Fc fusion protein application, it may be desired to either reduce or increase the effector function (such as ADCC).

For antibodies that target cell-surface molecules, especially those on immune cells, abrogating effector functions may be required for certain clinical indications.

Conversely, for antibodies intended for oncology use (such as in the treatment of leukemias and solid tumours; see below), increasing effector functions may improve the therapeutic activity.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns et al., 2009, *Blood.* 113(16):3716-25, the disclosures of which are incorporated herein by reference).

Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 of IgG2 residues at positions 233-236 and IgG4 residues at positions 327, 330 and 331 were shown to greatly reduce ADCC and CDC (Armour et al., 1999, *Eur J Immunol.* 29(8):2613-24; Shields et al., 2001, *J Biol Chem.* 276(9):6591-604, the disclosures of which are incorporated herein by reference). Furthermore, Idusogie et al. demonstrated that alanine substitution at different positions, including K322, significantly reduced complement activation (Idusogie et al., 2000, *J Immunol.* 164(8):4178-84, the disclosures of which are incorporated herein by reference). Similarly, mutations in the CH2 domain of murine IgG2A were shown to reduce the binding to FcγRI, and C1q (Steurer. et al., 1995. *J Immunol.* 155(3): 1165-74, the disclosures of which are incorporated herein by reference).

Numerous mutations have been made in the CH2 domain of human IgG1 and their effect on ADCC and CDC tested in vitro (see references cited above). Notably, alanine substitution at position 333 was reported to increase both ADCC and CDC (Shields et al., 2001, supra; Steurer et al., 1995, supra). Lazar et al. described a triple mutant (S239D/I332E/A330L) with a higher affinity for FcγRIIIa and a lower affinity for FcγRIIb resulting in enhanced ADCC (Lazar et al., 2006, *PNAS* 103(11):4005-4010, the disclosures of which are incorporated herein by reference). The same mutations were used to generate an antibody with increased ADCC (Ryan et al., 2007, *Mol. Cancer Ther.* 6:3009-3018, the disclosures of which are incorporated herein by reference). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards et al., 2008. *Mol Cancer Ther.* 7(8):2517-27, the disclosures of which are incorporated herein by reference).

Due to their lack of effector functions, IgG4 antibodies represent a preferred IgG subclass for receptor blocking without cell depletion (i.e. inhibition of IL-1 signalling). IgG4 molecules can exchange half-molecules in a dynamic process termed Fab-arm exchange. This phenomenon can also occur in vivo between therapeutic antibodies and endogenous IgG4.

The S228P mutation has been shown to prevent this recombination process allowing the design of less unpredictable therapeutic IgG4 antibodies (Labrijn et al., 2009, *Nat Biotechnol.* 27(8):767-71, the disclosures of which are incorporated herein by reference).

Examples of engineered Fc regions are shown in Table 1 and Example J below.

TABLE 1

Examples of Engineered Fc

| Isotype | Species | Mutations* | FcR/C1q Binding | Effector Function |
|---|---|---|---|---|
| IgG1 | Human | T250Q/M428L [1] | Increased binding to FcRn | increased half-life |
| IgG1 | Human | M252Y/S254T/T258E + H433K/N434F [2] | Increased binding to FcRn | Increased half-life |
| IgG1 | Human | M428L/N434S [3] | Increased binding to FcRn | Increased half-life |
| IgG1 | Human | E233P/L234V/L235A/?G236 + A327G/A330S/F331S [4,5] | Reduced binding to FcγRI | Reduced ADCC and CDC |
| IgG1 | Human | S239D/S298A/I332E + S239D/A330L/I332E [8] | Increased binding to FcγRIIIa | Increased ADCC |
| IgG1 | Human | S239D/I332E [7] | Increased binding to FcγRIIIa | Increased ADCC |
| IqG1 | Human | S298A/E333A/K334A [8] | Increased binding to FcγRIIIa | Increased ADCC |
| IgG1 | Human | E333A [9] | Increased binding to FcγRIIIa | Increased ADCC and CDC |
| IgG1 | Human | P257I/Q311 [10] | Increased binding to FcRn | Unchanged half-life |
| IgG1 | Human | K326W/E333S [11] | Increased binding to C1q | Increased CDC |
| IgG1 | Human | S239D/I332E/G236A [12] | increased FcγRIIa/ | Increased macrophage |

TABLE 1-continued

Examples of Engineered Fc

| Isotype | Species | Mutations* | FcR/C1q Binding | Effector Function |
|---|---|---|---|---|
| IgG1 | Human | K322A [8] | FcγRIIb ratio Reduced binding to C1q | phagocytosis Reduced CDC |
| | | N297S | | Reduced (abrogated) ADCC |
| | | N297Q | | Reduced (abrogated) ADCC |
| | | R292F + V305I +/− F243L [13] | | Increased ADCC |
| | | P247I/A339Q [14] | | Increased ADCC |
| IgG4 | Human | S228P [15] | — | Reduced Fab-arm exchange |
| IgG2a | Mouse | L238E + E318A/K320A/K322A [11] | Reduced binding to FcγRI and C1q | Reduced ADCC and CDC |

*The position of the Fc amino acid mutations is defined using the Eu Numbering Scheme, which differs from the numbering in SEQ ID NOS: 18 and 19 above; see Edelman et al., 1969, Proc. Natl. Acad. Sci. USA, 63: 78-85)

References to Table 1
[1] Hinton et al 2004 J. Biol. Chem. 279(8): 6213-6)
[2] Vaccaro et al. 2005 Nat Biotechnol. 23(10): 1283-8)
[3] Zalevsky et al 2010 Nat. Biotechnology 28(2): 157-159
[4] Armour K L. et al., 1999. Eur J Immunol. 29(8): 2613-24
[5] Shields R L. et al., 2001. J Biol Chem. 276(9): 6591-604
[6] Masuda et al. 2007, Mol Immunol. 44(12): 3122-31
[7] Bushfield et al 2014, Leukemia 28(11): 2213-21
[8] Okazaki et al. 2004, J Mol Biol.; 336(5): 1239-49
[9] Idusogie et al., 2000. J Immunol. 164(8): 4178-84
[10] Datta-Mannan A. et al., 2007. Drug Metab. Dispos. 35: 86-94
[11] Steurer W. et al., 1995. J Immunol. 155(3): 1165-74
[12] Richards et al. 2008 Mol Cancer There. 7(8): 2517-27
[13] U.S. Pat. No. 7,960,512 B2
[14] EP 2 213 683
[15] Labrijn A F. et al., 2009. Nat Biotechnol. 27(8): 767-71

In a further embodiment, the effector function of the Fc region may be altered through modification of the carbohydrate moieties within the CH2 domain therein.

For example, it is known that therapeutic antibodies lacking or low in fucose residues in the Fc region may exhibit enhanced ADCC activity in humans (for example, see Peipp et al., 2008, Blood 112(6):2390-9, Yamane-Ohnuki & Satoh, 2009, MAbs 1(3):230-26, Iida et al., 2009, BMC Cancer 9; 58 (the disclosures of which are incorporated herein by reference). Low fucose antibody polypeptides may be produced by expression in cells cultured in a medium containing an inhibitor of mannosidase, such as kinfunensine (see Example I below).

Other methods to modify glycosylation of an antibody into a low fucose format include the use of the bacterial enzyme GDP-6-deoxy-D-lyxo-4-hexulose reductase in cells not able to metabolise rhamnose (e.g. using the GlymaxX® technology of ProBioGen AG, Berlin, Germany).

Another method to create low fucose antibodies is by inhibition or depletion of alpha-(1,6)-fucosyltransferase in the antibody-producing cells (e.g. using the Potelligent® CHOK1SV technology of Lonza Ltd, Basel, Switzerland).

As noted above, the antibody polypeptides of the invention may exert an inhibitory action on IL-1 signalling (see Example E), either in addition to or in the absence of any Fc-mediated effector functions.

In one embodiment, the antibody polypeptides of the invention may exert an inhibitory action on one or more additional (or alternative) cytokines within the IL-1 superfamily, including but not limited to IL-33 and/or IL-36.

Interleukin-33 (IL-33) induces helper T cells, mast cells, eosinophils and basophils to produce type 2 cytokines. This cytokine was previously named NF-HEV 'nuclear factor (NF) in high endothelial venules' (HEVs) since it was originally identified in these specialized cells. IL-33 mediates its biological effects by interacting with the receptors ST2 (also known as IL1RL1) and IL-1 Receptor Accessory Protein (IL1RAP), activating intracellular molecules in the NF-κB and MAP kinase signaling pathways that drive production of type 2 cytokines (e.g. IL-5 and IL-1β) from polarised Th2 cells. The induction of type 2 cytokines by IL-33 in vivo is believed to induce the severe pathological changes observed in mucosal organs following administration of IL-33.

Interleukin-36 (IL-36) is a cytokine that predominantly acts on naive CD4+ T cells via the IL-36 receptor. It is known to activate NF-κB and mitogen-activated protein kinases to play a role in skin pathology. It has also been found to activate T cell proliferation and release of IL-2.

It will be appreciated by persons skilled in the art that the antibody polypeptide of the invention may inhibit IL-1, IL-33 and/or IL-36 signalling in whole or in part. For example, signalling may be inhibited by at least 10%, 20%, 30%, 50%, 75% or more relative to signalling in the absence of the polypeptide of the invention.

The degree of inhibition of IL-1, IL-33 and/or IL-36 signalling by the polypeptide of the invention may be determined using methods well known in the art.

For example, inhibition of IL-1 signalling may be measured as described in Example E below.

Likewise, inhibition of IL-33 signalling may be measured as described in Example E.

Inhibition of IL-36 signalling may be measured by methods known in the art. For example, IL-36 stimulation of synovial fibroblasts leads to NF-κB and MAP kinase activation. Alternatively, IL-36-α, -β and -γ increase T-cell proliferation in response to antiCD3/anti-CD28 stimulation (see Vigne et al., 2012, Blood 120(17):3478-87, the disclosures of which are incorporated herein by reference).

In one embodiment, the antibody or antigen-binding fragment thereof may further comprise a moiety for increasing the in vivo half-life of the antibody or antigen-binding fragment, such as but not limited to polyethylene glycol (PEG), human serum albumin, glycosylation groups, fatty acids and dextran. Such further moieties may be conjugated or otherwise combined with the binding moiety using methods well known in the art.

Any one or more of the following known methods of improving the half-life of proteins may be used for this purpose:

(a) PEGylation

A widely used method for improving the half-life of proteins is the covalent linking of polyethylene glycol (PEG) moieties to the protein. PEGs are water-soluble polymers that due to their large hydrodynamic volume create a shield around the pegylated drug [Molineux, G., Pegylation: engineering improved pharmaceuticals for enhanced therapy. Cancer Treat Rev, 2002. 28 Suppl A: p. 13-6, the disclosures of which are incorporated herein by reference]. Pegylated proteins exhibit a decreased renal clearance and proteolysis, reduced toxicity, reduced immunogenicity and an increased solubility [Veronese, F. M. and J. M. Harris, Introduction and overview of peptide and protein pegylation. Adv Drug Deliv Rev, 2002. 54(4): p. 453-6., Chapman, A. P., PEGylated antibodies and antibody fragments for improved therapy: a review. Adv Drug Deliv Rev, 2002. 54(4): p. 531-45.]. Pegylation has been employed for several protein-based drugs including the first pegylated molecules asparaginase and adenosine deaminase [Veronese, F. M. and J. M. Harris, *Introduction and overview of peptide and protein pegylation*. Adv Drug Deliv Rev, 2002. 54(4): p. 453-6, Veronese, F. M. and G. Pasut, *PEGylation, successful approach to drug delivery*. Drug Discov Today, 2005. 10(21): p. 1451-8, the disclosures of which are incorporated herein by reference].

In order to obtain a successfully pegylated protein, with a maximally increased half-life and retained biological activity, several parameters that may affect the outcome are of importance and should be taken into consideration. The PEG molecules may differ, and PEG variants that have been used for pegylation of proteins include PEG and monomethoxy-PEG. In addition, they can be either linear or branched [Wang, Y. S., et al., *Structural and biological characterization of pegylated recombinant interferon alpha-2b and its therapeutic implications*. Adv Drug Deliv Rev, 2002. 54(4): p. 547-70]. The size of the PEG molecules used may vary and PEG moieties ranging in size between 1 and 40 kDa have been linked to proteins [Wang, Y. S., et al., *Structural and biological characterization of pegylated recombinant interferon alpha-2b and its therapeutic implications*. Adv Drug Deliv Rev, 2002. 54(4): p. 547-70, Sato, H., Enzymatic procedure for site-specific pegylation of proteins. Adv Drug Deliv Rev, 2002. 54(4): p. 487-504, Bowen, S., et al., *Relationship between molecular mass and duration of activity of polyethylene glycol conjugated granulocyte colony-stimulating factor mutein*. Exp Hematol, 1999. 27(3): p. 425-32, Chapman, A. P., et al., *Therapeutic antibody fragments with prolonged in vivo half-lives*. Nat Biotechnol, 1999. 17(8): p. 780-3]. In addition, the number of PEG moieties attached to the protein may vary, and examples of between one and six PEG units being attached to proteins have been reported [Wang, Y. S., et al., *Structural and biological characterization of pegylated recombinant interferon alpha-2b and its therapeutic implications*. Adv Drug Deliv Rev, 2002. 54(4): p. 547-70, Bowen, S., et al., *Relationship between molecular mass and duration of activity of polyethylene glycol conjugated granulocyte colony-stimulating factor mutein*. Exp Hematol, 1999. 27(3): p. 425-32]. Furthermore, the presence or absence of a linker between PEG as well as various reactive groups for conjugation have been utilised. Thus, PEG may be linked to N-terminal amino groups, or to amino acid residues with reactive amino or hydroxyl groups (Lys, His, Ser, Thr and Tyr) directly or by using γ-amino butyric acid as a linker. In addition, PEG may be coupled to carboxyl (Asp, Glu, C-terminal) or sulfhydryl (Cys) groups. Finally, Gln residues may be specifically pegylated using the enzyme transglutaminase and alkylamine derivatives of PEG has been described [Sato, H., *Enzymatic procedure for site-specific pegylation of proteins*. Adv Drug Deliv Rev, 2002. 54(4): p. 487-504].

It has been shown that increasing the extent of pegylation results in an increased in vivo half-life. However, it will be appreciated by persons skilled in the art that the pegylation process will need to be optimised for a particular antibody polypeptide on an individual basis.

PEG may be coupled at naturally occurring disulphide bonds as described in WO 2005/007197, the disclosures of which are incorporated herein by reference. Disulfide bonds can be stabilised through the addition of a chemical bridge which does not compromise the tertiary structure of the protein. This allows the conjugating thiol selectivity of the two sulphurs comprising a disulfide bond to be utilised to create a bridge for the site-specific attachment of PEG. Thereby, the need to engineer residues into a peptide for attachment of to target molecules is circumvented.

A variety of alternative block copolymers may also be covalently conjugated as described in WO 2003/059973, the disclosures of which are incorporated herein by reference. Therapeutic polymeric conjugates can exhibit improved thermal properties, crystallisation, adhesion, swelling, coating, pH dependent conformation and biodistribution. Furthermore, they can achieve prolonged circulation, release of the bioactive in the proteolytic and acidic environment of the secondary lysosome after cellular uptake of the conjugate by pinocytosis and more favourable physicochemical properties due to the characteristics of large molecules (e.g. increased drug solubility in biological fluids). Co-block copolymers, comprising hydrophilic and hydrophobic blocks, form polymeric micelles in solution. Upon micelle disassociation, the individual block copolymer molecules are safely excreted.

(b) Fusion Proteins

Where the invention comprises or otherwise resides in the use of an antibody mimic (see above), the following types of fusion protein may be useful to extend half-life in vivo.

IgG Fusion Proteins

Human immunoglobulin G (IgG) molecules have circulating half-lives of approximately 20 days. The Fc portion of IgG molecules have been extensively used for the creation of fusion proteins consisting of an Fc part and a protein with a therapeutic use. Such fusion proteins exhibit a prolonged half-life compared to their Fc-lacking counterparts. For example, this strategy was used for the development of etanercept, an anti-rheumatic drug composed of a fusion protein between the soluble human p75 tumour necrosis factor receptor and the Fc portion of human IgG [Goldenberg, M. M., *Etanercept, a novel drug for the treatment of patients with severe, active rheumatoid arthritis*. Clin Ther, 1999. 21(1): p. 75-87; discussion 1-2, the disclosures of which are incorporated herein by reference].

Fc-linked proteins are produced by creating fusion proteins between Fc and the antigen-binding region of the polypeptide of interest by standard genetic engineering protocols. The Fc group is fused to the C-terminus of the protein of interest. Due to the presence of cysteine residues in the hinge region of IgG, Fc fusion proteins are expressed as disulfide-linked homodimers. This further increases their effective size and circulating half-lives. In addition, homodimeric constructs may have an increased functional activity due to improved avidity for its receptor/ligand compared to the corresponding monomeric form.

Human Serum Albumin Fusion Proteins

Human serum albumin (HSA) is the most abundant naturally occurring blood protein in the circulation and has a half-life of 19 days [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8, the disclosures of which are incorporated herein by reference]. Thus, HSA is a suitable fusion partner for the creation of fusion proteins with improved half-life. HSA fusion proteins exhibit a prolonged half-life due to the capability of HSA to stabilize the protein towards proteolysis and increasing the residence time in the body [Veronese, F. M. and J. M. Harris, *Introduction and overview of peptide and protein pegylation*. Adv Drug Deliv Rev, 2002. 54(4): p. 453-6]. HSA fusion proteins, including IL-2, IFN-α and -β and growth hormone (GH), have been produced and shown to have improved pharmacokinetic properties. Albuferon (HSA-IFN-α) and albutropin (HSA-GH) exhibit half-lives that are 18 and 6 times longer in cynomolgus monkeys, respectively, than the respective counterparts lacking an HSA group [Osborn, B. L., et al., *Pharmacokinetic and pharmacodynamic studies of a human serum albumin-interferon-alpha fusion protein in cynomolgus monkeys.* J Pharmacol Exp Ther, 2002. 303(2): p. 540-8, Osborn, B. L., et al., *Albutropin: a growth hormone-albumin fusion with improved pharmacokinetics and pharmacodynamics in rats and monkeys.* Eur J Pharmacol, 2002. 456(1-3): p. 149-58].

HSA-linked proteins are produced by creating fusion proteins between HSA and the protein of interest by standard genetic engineering protocols. The HSA group may be added at either the N- or the C-terminus. Since the modification is added to the terminus of the protein, the risk of interfering with the structure of the protein and thus with its function is considerably less compared to modifications such as pegylation in the interior of the protein. In addition, the chance of avoiding interference with the active site of the protein is increased by the fact that the HSA group may be added at either the N- or C-terminus of the protein of interest [Osborn, B. L., et al., *Pharmacokinetic and pharmacodynamic studies of a human serum albumin-interferon-alpha fusion protein in cynomolgus monkeys.* J Pharmacol Exp Ther, 2002. 303(2): p. 540-8, Osborn, B. L., et al., *Albutropin: a growth hormone-albumin fusion with improved pharmacokinetics and pharmacodynamics in rats and monkeys.* Eur J Pharmacol, 2002. 456(1-3): p. 149-58, Syed, S., K. E. Kelly, and W. P. Sheffield, *Inhibition of thrombin by hirudin genetically fused to wild-type or mutant antithrombin.* Thromb Res, 1996. 84(6): p. 419-29], depending on which is more likely to result in a fusion protein with maintained biological activity. Thus, in the case of albuferon and albutropin, the C-terminus of the HSA was fused with the N-terminus of IFN-α or GH, respectively, creation of a functionally active hirudin-HSA fusion protein, the HSA group had to be fused to the C-terminus of hirudin. These results indicate that the properties of the target protein determine whether fusion at the N- or C-terminus is optimal.

(c) Glycosylation

The introduction of new sialic acid-containing carbohydrates into a protein (glycoengineering) has been shown to improve in vivo half-life. This method may be used for naturally glycosylated proteins or for proteins that normally lack glycosylation [Elliott, S., et al., *Enhancement of therapeutic protein in vivo activities through glycoengineering.* Nat Biotechnol, 2003. 21(4): p. 414-21, the disclosures of which are incorporated herein by reference].

Glycosylation of proteins may be in the form of N-linked or O-linked carbohydrates. N-linked carbohydrates are typically attached to consensus sequences (Asn-X-Ser/Thr) where X is any amino acid except proline. O-glycosylation occurs at Ser/Thr residues.

For the production of glycosylated proteins, the introduction of novel glycosylation sites may be required. For glycosylation to occur, expression may be performed in yeast, insect or mammalian cell systems. However, the glycosylation pattern in yeast cells is different than mammalian cells, generating hyper-glycosylated proteins, associated with a risk of increased immunogenicity. In contrast, insect cells may be preferred since the glycosylation pattern is similar to that in mammalian cells whereas cell cycles are shorter and therefore expression process faster. Darbepoetin-α is an example of a modified human erythropoietin expressed in CHO cells. It contains two extra N-glycosylation sites, resulting in a three times improved in vivo half-life [Elliott, S., et al., *Enhancement of therapeutic protein in vivo activities through glycoengineering.* Nat Biotechnol, 2003. 21(4): p. 414-21].

An alternative method of glycosylation is the chemical addition of carbohydrate groups to proteins. In this method, the protein is expressed naked, e.g. in *E. coli*. Following expression and purification, the protein is glycosylated in a fully synthetic cell-free process. The method offers great flexibility in terms of number, size and type of carbohydrate to be added.

(d) Fatty Acid Acylation/Myristoylation

Fatty acids have a high affinity and high capacity of HSA binding. This characteristic can be utilized for improving the half-life of proteins. Thus, fatty acyl can be attached to amino acids of proteins, thus generating fatty acyl acylated proteins. Upon reaching the circulation, the fatty acyl group is capable of binding to circulating HSA, resulting in an improved in vivo half-life of the protein.

This method was used for the development of Insulin detemir, which was fatty acyl acylated with myristate at $Lys^{B29}$ by treatment of insulin with fatty acid hydroxylsuccinimide esters in dimethyl formamide/DMSO [Kurtzhals, P., et al., *Albumin binding of insulins acylated with fatty acids: characterization of the ligand-protein interaction and correlation between binding affinity and timing of the insulin effect in vivo.* Biochem J, 1995. 312 (Pt 3): p. 725-31, Hamilton-Wessler, M., et al., *Mechanism of protracted metabolic effects of fatty acid acylated insulin, NN304, in dogs: retention of NN304 by albumin.* Diabetologia, 1999. 42(10): p. 1254-63, the disclosures of which are incorporated herein by reference]. This generated an insulin analogue with increased in vivo half-life due to binding of HSA.

(e) Dextran

Dextran results in an immobilization of the protein, resulting in a slow release and thereby improves the half-life of the protein. Dextran-streptokinase, has been marketed in Russia for thrombolytic therapy. In addition, insulin, somatostatin (which is used for therapy and diagnosis of tumours expressing somatostatin receptors) and the ribosome-inactivating drug trichosantin conjugated to dextran, had a significantly improved half-lives [Baudys, M., et al., *Extending insulin action in vivo by conjugation to carboxymethyl dextran.* Bioconjug Chem, 1998. 9(2): p. 176-83, Chan, W. L., et al., *Lowering of trichosanthin immunogenicity by site—specific coupling to dextran.* Biochem Pharmacol, 1999. 57(8): p. 927-34, Wulbrand, U., et al., *A novel somatostatin conjugate with a high affinity to all five somatostatin receptor subtypes.* Cancer, 2002. 94(4 Suppl): p. 1293-7, the disclosures of which are incorporated herein by reference].

In addition to protein-based pharmaceuticals, dextran has been used for improving the half-life of antibiotics and cytotoxic drugs [Yura, H., et al., *Synthesis and pharmacokinetics of a novel macromolecular prodrug of Tacrolimus (FK506), FK506-dextran conjugate.* J Control Release, 1999. 57(1): p. 87-99, Nakashima, M., et al., *In vitro characteristics and in vivo plasma disposition of cisplatin conjugated with oxidized and dicarboxymethylated dextrans.* Biol Pharm Bull, 1999. 22(7): p. 756-61, Kim, D. S., Y. J. Jung, and Y. M. Kim, *Synthesis and properties of dextran-linked ampicillin.* Drug Dev Ind Pharm, 2001. 27(1): p. 97-101, the disclosures of which are incorporated herein by reference].

Dextran conjugation is carried out by reductive amination using periodate-activated dextran or by the use of cyanogens bromide [Wulbrand, U., et al., *A novel somatostatin conju-* gate with a high affinity to all five somatostatin receptor subtypes. Cancer, 2002. 94(4 Suppl): p. 1293-7, Kim, D. S., Y. J. Jung, and Y. M. Kim, *Synthesis and properties of dextran-linked ampicillin*. Drug Dev Ind Pharm, 2001. 27(1): p. 97-101, the disclosures of which are incorporated herein by reference]. The dextran used may vary in size, and dextran ranging from 9 to 82 kDa have been used [Kim, D. S., Y. J. Jung, and Y. M. Kim, *Synthesis and properties of dextran-linked ampicillin*. Drug Dev Ind Pharm, 2001. 27(1): p. 97-101, Behe, M., et al., *Biodistribution, blood half-life, and receptor binding of a somatostatin-dextran conjugate*. Med Oncol, 2001. 18(1): p. 59-64, the disclosures of which are incorporated herein by reference].

In addition to improving the half-life of drugs, dextran conjugation may also reduce immunogenicity [Chan, W. L., et al., *Lowering of trichosanthin immunogenicity by site-specific coupling to dextran*. Biochem Pharmacol, 1999. 57(8): p. 927-34, the disclosures of which are incorporated herein by reference].

Thus, in one embodiment of the first aspect of the invention, the polypeptide of the invention is or comprises a "fusion" polypeptide.

In addition to being fused to a moiety in order to improve pharmacokinetic properties, it will be appreciated that the polypeptide of the invention may also be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag, such as His6, or to an epitope recognised by an antibody such as the well-known Myc tag epitope. Fusions to any variant or derivative of said polypeptide are also included in the scope of the invention. It will be appreciated that fusions (or variants, derivatives or fusions thereof) which retain or improve desirable properties, such as IL-1R binding properties or in vivo half-life are preferred.

Thus, the fusion may comprise an amino acid sequence as detailed above together with a further portion which confers a desirable feature on the said polypeptide of the invention; for example, the portion may useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

It will be appreciated by persons skilled in the art that the antibody polypeptides of the invention may comprise or consist of one or more amino acids which have been modified or derivatised. Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudo-peptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will also be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

The antibody polypeptides of the invention may be augmented with a functional moiety to facilitate their intended use, for example as a diagnostic (e.g. in vivo imaging) agent or therapeutic agent. Thus, in one embodiment, the antibody polypeptide is linked, directly or indirectly, to a therapeutic moiety.

In one embodiment, the antibody or antigen-binding fragment thereof according to any one of the preceding claim further comprising a therapeutic (e.g. cytotoxic) moiety.

Any suitable therapeutic moiety may be used. A suitable therapeutic moiety is one that is capable of reducing or inhibiting the growth, or in particular killing, a cancer cell (or associated stem cells or progenitor cells). For example, the therapeutic agent may be a cytotoxic moiety. The cytotoxic moiety may comprise or consist of one or more radioisotopes. For example, the one or more radioisotopes may each be independently selected from the group consisting of beta-emitters, Auger-emitters, conversion electron-emitters, alpha-emitters, and low photon energy-emitters. It may be desired that the one or more radioisotopes each independently has an emission pattern of locally absorbed energy that creates a high absorbed dose in the vicinity of the agent. Exemplary radioisotopes may include long-range beta-emitters, such as $^{90}$Y, $^{32}$P, $^{186}$Re/$^{188}$Re; $^{166}$Ho, $^{76}$As/$^{77}$As, $^{89}$Sr, $^{153}$Sm; medium range beta-emitters, such as $^{131}$I, $^{177}$Lu, $^{67}$Cu, $^{161}$Tb, $^{105}$Rh; low-energy beta-emitters, such as $^{45}$Ca or $^{35}$S; conversion or Auger-emitters, such as $^{51}$Cr, $^{67}$Ga, $^{99}$Tc$^m$, $^{111}$In, $^{114m}$In $^{123}$I, $^{125}$I, $^{201}$Tl; and alpha-emitters, such as $^{212}$Bi, $^{213}$Bi, $^{223}$Ac, $^{225}$Ac, $^{212}$Pb, $^{255}$Fm, $^{223}$Ra, $^{149}$Tb and $^{221}$At. Other radionuclides are available and will be possible to use for therapy.

In one preferred embodiment, the antibody polypeptide is linked to (or otherwise labelled with) the radioisotope $^{177}$Lu.

Alternatively, the therapeutic moiety may comprise or consist of one or more therapeutic (such as cytotoxic) drugs, for example, a cytostatic drug; an anti-androgen drug; cortisone and derivatives thereof; a phosphonate; a testosterone-5-α-reductase inhibitor; a boron addend; a cytokine; thapsigargin and its metabolites; a toxin (such as saporin or calicheamicin); a chemotherapeutic agent (such as an anti-metabolite); or any other therapeutic or cytotoxic drug useful in the treatment of cancers.

Exemplary therapeutic/cytotoxic drugs may, for example, include:

Cytostatics, in particular those with dose-limiting side-effects, including but not limited to cyclophosamide, chlorambucil, ifosfamide, busulphane, lomustine, taxanes, estramustine phosphate and other nitrogen mustards, antibiotics (including doxorubicine, calicheamicines and esperamicine), vinca alkaloids, azaridines, platinum-containing compounds, endostatin, alkyl sulfonates, nitrosoureas, triazenes, folic acid analoges, pyrimidine analoges, purine analogs, enzymes, substituted urea, methyl-hydrazine derivatives, daunorubicin, amphipathic amines, Anti-androgens such as flutamide and bikalutamide and metabolites thereof;

Cortisone and derivatives thereof;

Phosphonates such as diphophonate and buphosphonate;

Testosterone-5-α-reductase inhibitors;

Boron addends;

Cytokines;

Thapsigargin and its metabolites.

Alternatively, the cytotoxic moiety may comprise or consist of one or more moieties suitable for use in activation therapy, such as photon activation therapy, neutron activation therapy, neutron-induced Auger electron therapy, synchrotron irradiation therapy or low energy X-ray photon activation therapy.

For example, with the antibody polypeptides of the invention there will be the potential of using synchrotron radiation (or low energy X-rays) for the advancement of radiotherapy, primarily focusing on so called photo-activation radio-therapy (PAT), in which the local energy deposition from external X-ray irradiation is enhanced in the cancer tissue by the interaction with a pre-administered, high-Z tumour-targeting agent.

The PAT treatment modality utilises monochromatic X-rays from a synchrotron source, such as provided by the ID17 biomedical beamline at the European Synchrotron Radiation Facility (ESRF) in Grenoble, and as anticipated to be available at other facilities in the future such as the new Swedish synchrotron facility, Max-IV.

Research on "induced Auger electron tumour therapy", to be conducted at the coming European Spallation Source (ESS) in Lund, provides a further potential treatment modality. Reactor-produced thermal and semi-thermal neutrons have for long been used for Boron-Neutron-Capture-Therapy, BNCT, both for pre-clinical experiments and for treatment of brain tumours with the induced alpha-particles and the recoil nucleus ($^7$L) that give a high locally absorbed energy. A similar approach is to use neutrons and suitable tumour-targeting molecules labelled with stable nuclei with high cross-section for neutrons. Antibodies or peptides can for instance be labelled with stable Gadolinium ($^{157}$Gd) and act as the target molecule for the neutrons that are captured by the Gd-nucleus, so called *Gadolinium Neutron Capture Therapy (GdNCT)*. By Monte Carlo techniques, the dose distribution in the tumour and the surrounding tissues is calculated as it results from γ-photons, neutrons, nuclear recoils, as well as characteristic x-rays, internal conversion and Auger-electrons from gadolinium or other potential elements.

Optionally, the antibody polypeptide of the invention may further comprise a detectable moiety.

For example, a detectable moiety may comprise or consist of a radioisotope, such as a radioisotope selected from the group consisting of $^{99m}$Tc, $^{111}$In, $^{67}$Ga, $^{68}$Ga, $^{72}$As, $^{89}$Zr, $^{123}$I and $^{201}$Tl Optionally, the agent may comprise a pair of detectable and cytotoxic radionuclides, such as $^{86}$Y/$^{90}$Y or $^{124}$I/$^{211}$At. Alternatively, the antibody polypeptide may comprise a radioisotope that is capable of simultaneously acting in a multi-modal manner as a detectable moiety and also as a cytotoxic moiety to provide so-called "Multimodality theragnostics". The binding moieties may thus be coupled to nanoparticles that have the capability of multi-imaging (for example, SPECT, PET, MRI, Optical, or Ultrasound) together with therapeutic capability using cytotoxic drugs, such as radionuclides or chemotherapy agents.

Alternatively, the detectable moiety may comprise or consist of a paramagnetic isotope, such as a paramagnetic isotope is selected from the group consisting of $^{157}$Gd, $^{55}$Mn, $^{162}$Dy, $^{52}$Cr and $^{56}$Fe.

In the case that the antibody polypeptide comprises a detectable moiety, then the detectable moiety may be detectable by an imaging technique such as SPECT, PET, MRI, optical or ultrasound imaging.

Therapeutic and/or detectable moieties (such as a radioisotope, cytotoxic moiety or the like) may be linked directly, or indirectly, to the antibody or fragment thereof. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-tri-acetic acid (NOTA) and derivatives of 1,4,8,11-tetraazacyclodocedan-1,4,8,11-tetraacetic acid (TETA), derivatives of 3,6,9,15-Tetraazabicyclo[9.3.1]-pentadeca-1(15),11,13-triene-4-(S)-(4-isothiocyanato-benzyl)-3,6,9-tri-acetic acid (PCTA), derivatives of 5-S-(4-Aminobenzyl)-1-oxa-4,7,10-triazacyclododecane-4,7,10-tris(acetic acid) (DO3A) and other chelating moieties.

One preferred linker is DTPA, for example as used in $^{177}$Lu-DTPA-[antibody polypeptide of the invention]. A further preferred linker is deferoxamine, DFO, for example as used in $^{89}$Zr-DFO-[antibody polypeptide of the invention].

However, it will be appreciated by persons skilled in the art that some medical uses of the antibody polypeptides of the invention will not require the presence of a cytotoxic or diagnostic moiety.

Thus, where the therapeutic effect of the antibody of the invention is mediated by inhibition of IL-1 signalling (or IL-33 and/or IL-36 signalling), a 'naked' antibody polypeptide may be suitable. For example, where the therapeutic effect is mediated by a direct effect of the antibody of the invention on immune cells, e.g. to reduce inflammation, it may be advantageous for the antibody to lack any cytotoxic activity.

As discussed above, methods for the production of antibody polypeptides of the invention are well known in the art.

Conveniently, the antibody polypeptide is or comprises a recombinant polypeptide. Suitable methods for the production of such recombinant polypeptides are well known in the art, such as expression in prokaryotic or eukaryotic hosts cells (for example, see Green & Sambrook, 2012, *Molecular Cloning, A Laboratory Manual*, Fourth Edition, Cold Spring Harbor, N.Y., the relevant disclosures in which document are hereby incorporated by reference).

Antibody polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that antibody polypeptides of the invention may alternatively be synthesised artificially, for example using well known liquid-phase or solid phase synthesis techniques (such as t-Boc or Fmoc solid-phase peptide synthesis).

A second aspect of the invention provides an isolated nucleic acid molecule encoding an antibody or antigen-binding fragment of the first aspect of the invention, or a component polypeptide chain thereof. By "nucleic acid molecule" we include DNA (e.g. genomic DNA or complementary DNA) and mRNA molecules, which may be single- or double-stranded. By "isolated" we mean that the nucleic acid molecule is not located or otherwise provided within a cell.

In one embodiment, the nucleic acid molecule is a cDNA molecule.

It will be appreciated by persons skilled in the art that the nucleic acid molecule may be codon-optimised for expression of the antibody polypeptide in a particular host cell, e.g. for expression in human cells (for example, see Angov, 2011, *Biotechnol. J.* 6(6):650-659, the disclosures of which are incorporated herein by reference).

Also included within the scope of the invention are the following:
  (a) a third aspect of the invention provides a vector (such as an expression vector) comprising a nucleic acid molecule according to the second aspect of the invention;
  (b) a fourth aspect of the invention provides a host cell (such as a mammalian cell, e.g. human cell, or Chinese hamster ovary cell, e.g. CHOK1SV cells) comprising a nucleic acid molecule according to the second aspect of the invention or a vector according to the third aspect of the invention; and
  (c) a fifth aspect of the invention provides a method of making an antibody polypeptide according to the first aspect of the invention comprising culturing a population of host cells according to the fourth aspect of the invention under conditions in which said polypeptide is expressed, and isolating the polypeptide therefrom.

A sixth aspect of the invention provides a pharmaceutical composition comprising a pharmaceutically effective amount of an antibody or antigen-binding fragment according to the first aspect of the invention and a pharmaceutically-acceptable diluent, carrier, adjuvant or excipient.

It will be appreciated by persons skilled in the art that additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the IL1RAP-binding activity of the antibody polypeptide of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the antibody polypeptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the antibody polypeptide of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The antibody polypeptides of the invention may be formulated into any type of pharmaceutical composition known in the art to be suitable for the delivery thereof.

In one embodiment, the pharmaceutical compositions of the invention may be in the form of a liposome, in which the antibody polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the antibody polypeptide may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active antibody polypeptide. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the antibody polypeptides of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the antibody polypeptides of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the antibody polypeptide of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

In the context of diagnostic use of the antibody polypeptides of the invention, a 'pharmaceutically effective amount', or 'effective amount', or 'diagnostically effective', as used herein, refers to that amount which provides a detectable signal for diagnosis, e.g. for in vivo imaging purposes.

The antibody polypeptides can be formulated at various concentrations, depending on the efficacy/toxicity of the polypeptide being used. For example, the formulation may comprise the active antibody polypeptide at a concentration of between 0.1 µM and 1 mM, more preferably between 1 µM and 500 µM. between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM, between 500 µM and 600 µM, between 600 µM and 700 µM, between 800 µM and 900 µM or between 900 µM and 1 mM. Typically, the formulation comprises the active antibody polypeptide at a concentration of between 300 µM and 700 µM.

Typically, the therapeutic dose of the antibody polypeptide (with or without a therapeutic moiety) in a human patient will be in the range of 100 µg to 1 g per administration (based on a body weight of 70 kg, e.g. between 300 µg to 700 mg per administration). For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

It will be appreciated by persons skilled in the art that the pharmaceutical compositions of the invention may be administered alone or in combination with other therapeutic agents used in the treatment of cancers, such as antimetabolites, alkylating agents, anthracyclines and other cytotoxic antibiotics, *vinca* alkyloids, etoposide, platinum compounds, taxanes, topoisomerase I inhibitors, antiproliferative immunosuppressants, corticosteroids, sex hormones and hormone antagonists, and other therapeutic antibodies (such as trastuzumab).

It will be further appreciated by persons skilled in the art that the polypeptides and pharmaceutical formulations of the present invention have utility in both the medical and veterinary fields. Thus, the methods of the invention may be used in the treatment of both human and non-human animals (such as horses, dogs and cats). Preferably, however, the patient is human.

For veterinary use, a compound of the invention is administered as a suitably acceptable formulation in accordance with normal veterinary practice and the veterinary surgeon will determine the dosing regimen and route of administration which will be most appropriate for a particular animal.

A seventh aspect of the invention provides an antibody or antigen-binding fragment thereof according to the first aspect of the invention for use in medicine.

In one embodiment, the antibody polypeptides and formulations of the invention may be used to treat patients or subjects who suffer from or are at risk of suffering from a disease or indication for which IL1RAP is a biomarker.

Thus, a related eighth aspect of the invention provides an antibody or antigen-binding fragment thereof according to the first aspect of the invention for use in inducing cell death and/or inhibiting the growth and/or proliferation of pathological cells associated with a neoplastic disorder in a subject, or stem cells or progenitor cells thereof, wherein the cells express IL1RAP.

A further related ninth aspect of the invention provides an antibody or antigen-binding fragment according to the first aspect of the invention for use in the treatment and/or diagnosis of a neoplastic disorder in a subject, wherein the neoplastic disorder is associated with cells expressing IL1RAP.

By 'treatment' we include both therapeutic and prophylactic treatment of the patient. The term 'prophylactic' is used to encompass the use of an agent, or formulation thereof, as described herein which either prevents or reduces the likelihood of a neoplastic disorder, or the spread, dissemination, or metastasis of cancer cells in a patient or subject. The term 'prophylactic' also encompasses the use of an agent, or formulation thereof, as described herein to prevent recurrence of a neoplastic disorder in a patient who has previously been treated for the neoplastic disorder.

By "diagnosis" we include the detection of cancerous cells, either in vivo (i.e. within the body of a patient) or ex vivo (i.e. within a tissue or cell sample removed from the body of a patient).

By "a neoplastic disorder associated with cells expressing IL1RAP" we include such disorders wherein the pathological cells which are responsible, directly or indirectly, for the disorder express IL1RAP on the cell surface. It will be appreciated that the cells expressing IL1RAP may be cancer cells, e.g. tumour cells, per se. In addition, such cells include pathological stem cells (i.e. cancer stem cells, or CSCs) and progenitor cells which are responsible, directly or indirectly, for the development of a neoplastic disorder in an individual. Examples of CSCs are disclosed in Visvader & Lindeman, 2008, *Nat Rev Cancer* 8:755-768, the disclosures of which are incorporated herein by reference.

Alternatively, or in addition, the cells expressing IL1RAP may be associated indirectly with the neoplastic disorder, for example, they may mediate cellular processes required for the neoplastic cells to survive. The antibody agent of the invention may in this event target cells essential for the blood supply of the tumour (angiogenesis) or cells inhibiting a beneficial immune response directed against the malignant cells (e.g. suppressive macrophages or T-cells).

Depending upon whether it is therapeutically desirable to kill the target cells expressing IL1RAP, an antibody or antigen-binding fragment according to the first aspect of the invention may be used that it capable of inducing ADCC. For example, where the target cells IL1RAP are cancer cells (such as CML, AML, ALL, melanoma, lung cancer cells, etc) it may be advantageous for the antibody or antigen-binding fragment to be capable of inducing ADCC in order to eliminate such cells. However, it will be appreciated that a therapeutic benefit may also be achieved using an antibody or antigen-binding fragment that lacks ADCC activity, for example through inhibition of IL-1 (or IL-33 or IL-36) signalling leading to reduced angiogenesis in the vicinity of a tumour.

In one embodiment, the neoplastic disorder is a neoplastic hematologic disorder.

For example, the antibody or antigen-binding fragment thereof may be for use in the treatment and/or diagnosis of a neoplastic disorder selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In a further embodiment, the antibody or antigen-binding fragment thereof is for use in the treatment and/or diagnosis of a neoplastic disorder associated with the formation of solid tumours within the subject's body.

Thus, the antibody or antigen-binding fragment thereof may be for use in the treatment of a neoplastic disorder selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer, and sarcomas.

In relation to the therapeutic and prophylactic aspects of the invention, it will be appreciated by persons skilled in the art that binding of the antibody polypeptide to IL1RAP present on the surface of the cells associated with the neoplastic disorder may lead to a modulation (i.e. an increase or decrease) of a biological activity of IL1RAP. However, such a modulatory effect is not essential; for example, the antibody polypeptides of the invention may elicit a therapeutic and prophylactic effect simply by virtue of binding to IL1RAP on the surface of the cells associated with the solid tumour, which in turn may trigger the immune system to induce cell death (e.g. by ADCC and/or by the presence within the agent of a cytotoxic/radioactive moiety).

By "biological activity of IL1RAP" we include any interaction or signalling event which involves IL1RAP on the cells associated with the neoplastic disorder. For example, in one embodiment the antibody polypeptide is capable of blocking binding of one or more co-receptors to IL1RAP (such as IL1R1, ST2, C-KIT and/or IL1RL2).

Such inhibition of the biological activity of IL1RAP by an antibody polypeptide of the invention may be in whole or in part. For example, the agent may inhibit the biological activity of IL1RAP by at least 10%, preferably at least 20%, 30%, 40%, 50%, 60%, 70%, 80% or 90%, and most preferably by 100% compared to the biological activity of IL1RAP in cells associated with the neoplastic disorder which have not been exposed to the antibody polypeptide. In a preferred embodiment, the antibody polypeptide is capable of inhibiting the biological activity of IL1RAP by 50% or more compared to the biological activity of IL1RAP in cells associated with the neoplastic disorder which have not been exposed to the antibody polypeptide.

Likewise, it will be appreciated that inhibition of growth and/or proliferation of the cells associated with the neoplastic disorder may be in whole or in part. For example, the antibody polypeptide may inhibit the growth and/or proliferation of the cells associated with the neoplastic disorder by at least 10%, preferably at least 20%, 30%, 40%, 50%, 60%, 70%, 80% or 90%, and most preferably by 100% compared to the growth and/or proliferation of cells associated with the neoplastic disorder which have not been exposed to the antibody polypeptide.

A tenth aspect of the invention provides an of an antibody or antigen-binding fragment thereof according to the first aspect of the invention in the preparation of a medicament for the treatment or diagnosis of a neoplastic disorder in a subject, wherein the neoplastic disorder is associated with cells expressing IL1RAP.

In one embodiment, the neoplastic disorder is a neoplastic hematologic disorder.

For example, the antibody or antigen-binding fragment thereof may be for use in the treatment and/or diagnosis of a neoplastic disorder selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In a further embodiment, the antibody or antigen-binding fragment thereof is for use in the treatment and/or diagnosis of a neoplastic disorder associated with the formation of solid tumours within the subject's body.

Thus, the antibody or antigen-binding fragment thereof may be for use in the treatment of a neoplastic disorder selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer, and sarcomas.

An eleventh aspect of the invention provides a method for the treatment or diagnosis of a neoplastic disorder in a subject, comprising the step of administering to the subject an effective amount of an antibody or antigen-binding fragment thereof according to the first aspect of the invention, wherein the neoplastic disorder is associated with cells expressing IL1RAP.

In one embodiment, the neoplastic disorder is a neoplastic hematologic disorder.

For example, the method may be for use in the treatment and/or diagnosis of a neoplastic disorder selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In a further embodiment, the method is for use in the treatment and/or diagnosis of a neoplastic disorder associated with the formation of solid tumours within the subject's body.

Thus, the method may be for use in the treatment of a neoplastic disorder selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer, and sarcomas.

In a further embodiment, the antibody polypeptides and formulations of the invention may be used to treat patients or subjects who suffer from or are at risk of suffering a disease or condition susceptible to treatment with an inhibitor of IL-1 (or IL-33 or IL-36) signalling.

Thus, a twelfth aspect of the invention provides an antibody or antigen-binding fragment thereof according to the first aspect of the invention for use in the treatment of a disease or condition susceptible to treatment with an inhibitor of IL-1 signalling.

Such conditions or disease states are well known in the art (see Dinarello et al., 2012, *Nature Reviews* 11:633-652 and Dinarello, 2014, *Mol. Med.* 20(suppl. 1):S43-S58, the disclosures of which are incorporated herein by reference) and include, but are not limited to, the following:

Rheumatoid arthritis, all types of juvenile arthritis including systemic onset juvenile idiopathic arthritis (SO-JIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, psoriasis, asthma, atherosclerosis, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease (including ulcerative colitis and Crohn's disease), Hepatitis C, ischaemia-reperfusion injury, multiple sclerosis, Neisserial or pneumococcal meningitis, tuberculosis, Bechet's syndrome, septic shock, graft versus host disease, asthma, type I diabetes, Alzheimer's disease, atherosclerosis, adult T cell leukaemia, multiple myeloma, periodontitis, obesity and obesity-related diseases (for example, metabolic syndrome, cardiomegaly, congestive heart failure, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis and gout.

Blockade of IL-1 signalling is also believed to be beneficial in the treatment of myocardial infarction. An extensive clinical trial is currently seeking to confirm the efficacy of IL1B antibody blockade (using Canakinumab) following myocardial infarction (the CANTOS trail; see Ridker et al., 2011, *Am Heart Journal* 162(4):597-605, the disclosures of which are incorporated herein by reference).

For such indications, it will be appreciated that a therapeutic benefit may also be achieved using an antibody or antigen-binding fragment that binds IL1RAP and thereby blocking IL-1 (or IL-33 or IL-36) signalling associated with immune cells. Such antibody could be modified to lack ADCC activity.

A thirteenth aspect of the invention provides the use of an antibody or antigen-binding fragment thereof according to the first aspect of the invention in the preparation of a medicament for the treatment of a disease or condition susceptible to treatment with an inhibitor of IL-1 (or IL_33 or IL-36) signalling.

A fourteenth aspect of the invention provides a method for the treatment of a disease or condition susceptible to treatment with an inhibitor of IL-1 (or IL_33 or IL-36) signalling in a subject, comprising the step of administering to the subject an effective amount of an antibody or antigen-binding fragment thereof according to the first aspect of the invention.

A fifteenth aspect of the invention provides a method for the ADCC-mediated treatment or augmentation of a disease or condition susceptible to treatment with an inhibitor of IL-1 (or IL-33 or IL-36) signalling in a subject, comprising the step of administering to the subject an effective amount of an antibody or antigen-binding fragment thereof according to the first aspect of the invention capable of inducing ADCC.

A sixteenth aspect of the invention provides an in vitro method for the detection of cancer cells in a subject, the method comprising:
(a) providing a sample of cells (e.g. white blood stem/progenitor cells or biopsy tissue) from a subject to be tested;
(b) optionally, extracting and/or purifying the cells present in the sample;
(c) contacting an antibody or antigen-binding fragment thereof according to the first aspect of the invention with cells present in the sample;
(d) determining whether the antibody polypeptide binds to the cells wherein the binding of the antibody polypeptide to the cells is indicative of the presence of cancer cells in the tissue of a subject.

A seventeenth aspect of the invention provides an in vitro method for identifying a patient with cancer who would benefit from treatment with an antibody or antigen-binding fragment thereof according to the first aspect of the invention, the method comprising:
(a) providing a sample of cancer cells (e.g. white blood stem/progenitor cells or biopsy tissue) from a patient to be tested;

(b) optionally, extracting and/or purifying the cells present in the sample;
(c) contacting an antibody or antigen-binding fragment thereof according to the first aspect of the invention with cells present in the sample;
(d) determining whether the antibody polypeptide binds to the cells wherein the binding of the antibody polypeptide to the cancer cells is indicative of a patient who would benefit from treatment with an antibody or antigen-binding fragment thereof according to the first aspect of the invention.

Persons skilled in the art will appreciate that there are many ways to perform such an assay. For example, the immunoassay could be either homogeneous or, more preferably, heterogeneous. The assay could also be performed in either a competitive or, more preferably, a non-competitive format.

In one embodiment, IL1RAP expression on blood samples (leukemia) or biopsies (solid tumours) from patients is measured using flow cytometry or immunohistochemistry, with expression above a threshold value being indicative of a patient who would benefit from treatment with an antibody or antigen-binding fragment thereof according to the first aspect of the invention.

In preferred embodiments of the above in vitro methods, step (d) is performed by flow cytometry, immunohistochemistry or ELISA.

However, other assays suitable for detecting antibody-antigen interactions in vitro may be used.

A eighteenth aspect of the invention provides a method for treating a patient with cancer, the method comprising administering to a subject identified as having cancer using a method according to the sixteenth or seventeenth aspects of the invention a therapeutic agent effective in the treatment of said cancer. In one embodiment, the example therapeutic agent is an antibody polypeptide according to the first aspect of the invention.

In one embodiment, the method comprises:
(a) arranging for a sample of cells (e.g. white blood stem/progenitor cells or biopsy tissue) from a subject to be tested for the presence of cancer cells expressing IL1RAP above a threshold criteria using a method according to the sixteenth or seventeenth aspect of the invention;
(b) selecting for treatment subjects whose sample of cells tested in step (a) contains cancer cells with IL1RAP expression above a threshold criteria; and
(c) administering to the subject selected in step (b) a therapeutic agent effective in the treatment of said cancer, for example an antibody polypeptide according to the first aspect of the invention.

In a related embodiment, the method comprises:
(a) obtaining a sample of cells (e.g. white blood stem/progenitor cells or biopsy tissue) from a subject
(b) testing said cells for the presence of cancer cells expressing IL1RAP above a threshold criteria using a method according to the sixteenth or seventeenth aspect of the invention;
(c) selecting for treatment subjects whose sample of cells tested in step (b) contains cancer cells with IL1RAP expression above a threshold criteria; and
(d) administering to the subject selected in step (c) a therapeutic agent effective in the treatment of said cancer, for example an antibody polypeptide according to the first aspect of the invention.

Preferences and options for a given aspect, feature or parameter of the invention should, unless the context indicates otherwise, be regarded as having been disclosed in combination with any and all preferences and options for all other aspects, features and parameters of the invention. For example, in one embodiment the invention provides an intact IgG1 antibody comprising a heavy chain variable region having the amino acid sequence of SEQ ID NO:9 and a light chain variable region having the amino acid sequence of SEQ ID NO:16 for use in the treatment of AML.

The listing or discussion of an apparently prior-published document in this specification should not necessarily be taken as an acknowledgement that the document is part of the state of the art or is common general knowledge.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

FIG. 1. Binding of the exemplary antibody in an indirect ELISA to human IL-1RAP. The exemplary antibody of the invention, CAN04, was found to possess the highest affinity for human IL-1RAP.

Figure 2A:
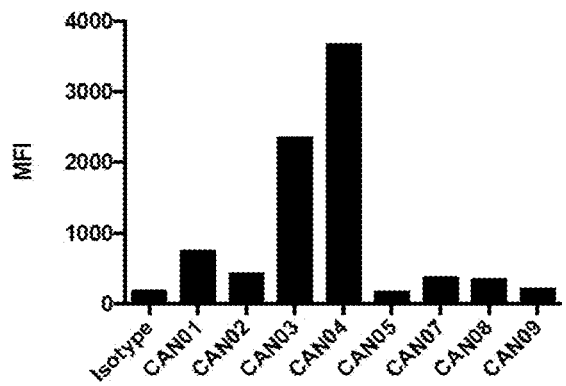
Figure 2B:
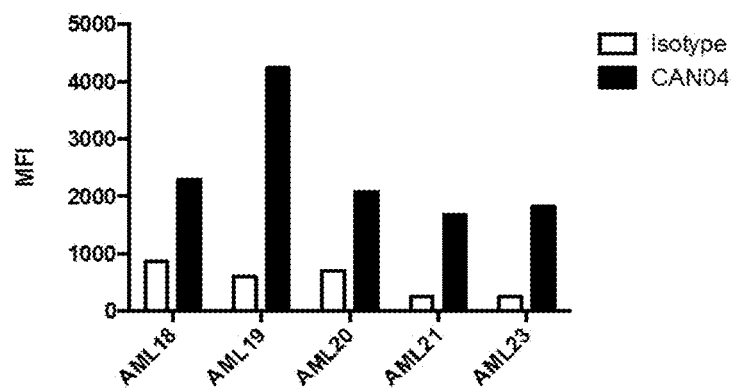
Figure 2C:
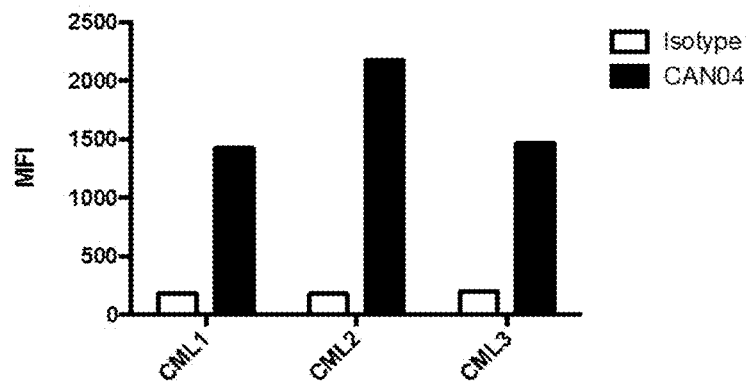

FIGS. 2A-C. Binding of exemplary antibody of the invention (CAN04) to human CML and AML cells. (2A) The graph shows the MFI value for KU812 cells stained with IL1RAP-targeting monoclonal antibodies at a concentration of 0.1 μg/1 mL, and reveals that CAN04 has the highest MFI of the compared antibodies. (2B) CAN04 shows specific binding to five primary AML samples. (2C) In three primary CML samples, CAN04 shows specific binding.

Figure 3:
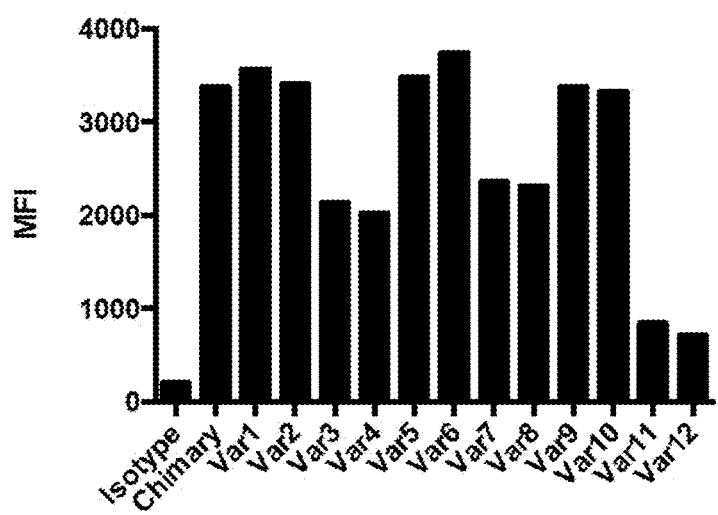

FIG. 3. Exemplary humanized variants of antibody CAN04 all bind to IL1RAP-expressing BV173 cells, with Variant 6 showing the highest mean fluorescent intensity.

Figure 4A:
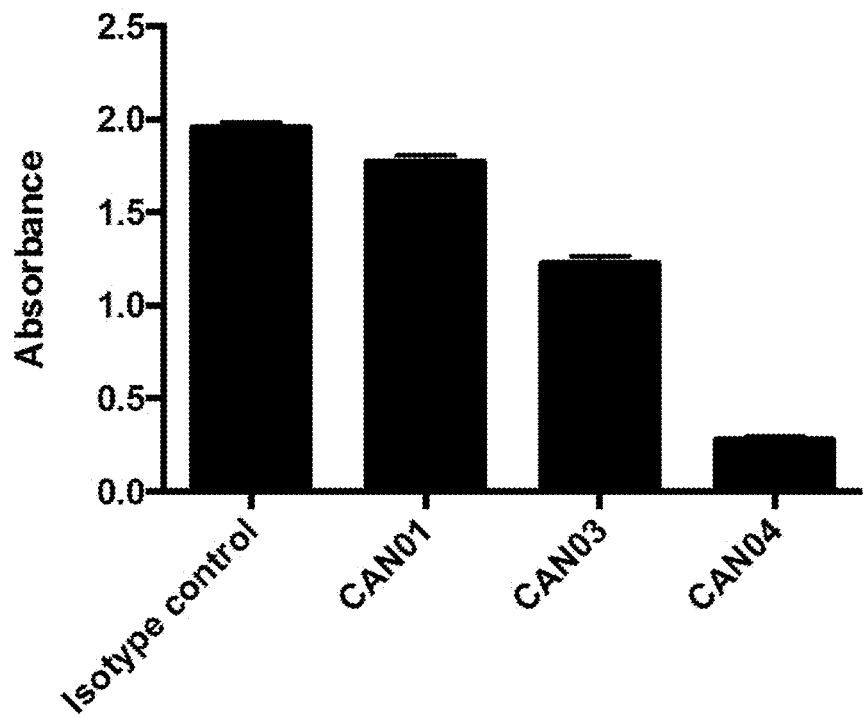
Figure 4B:
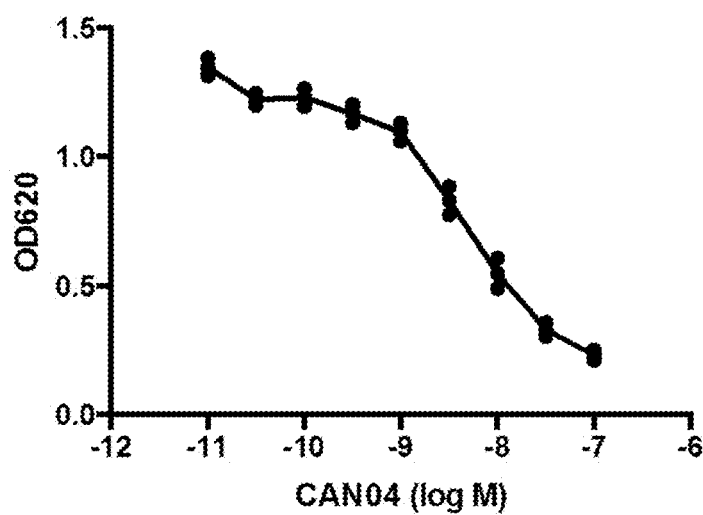
Figure 4C:
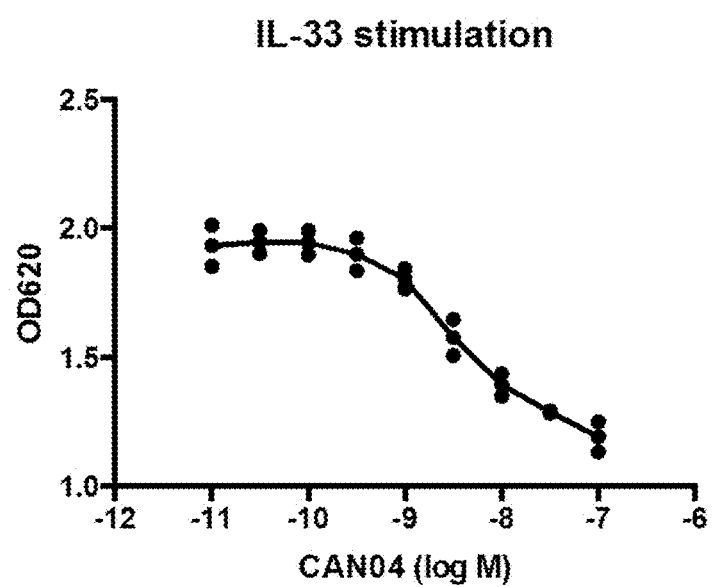

FIGS. 4A-C. Ability of exemplary antibody CAN04 to block (4A) IL-1β (4B) IL-1α, and (4C) IL-33 signalling.

Figure 5:
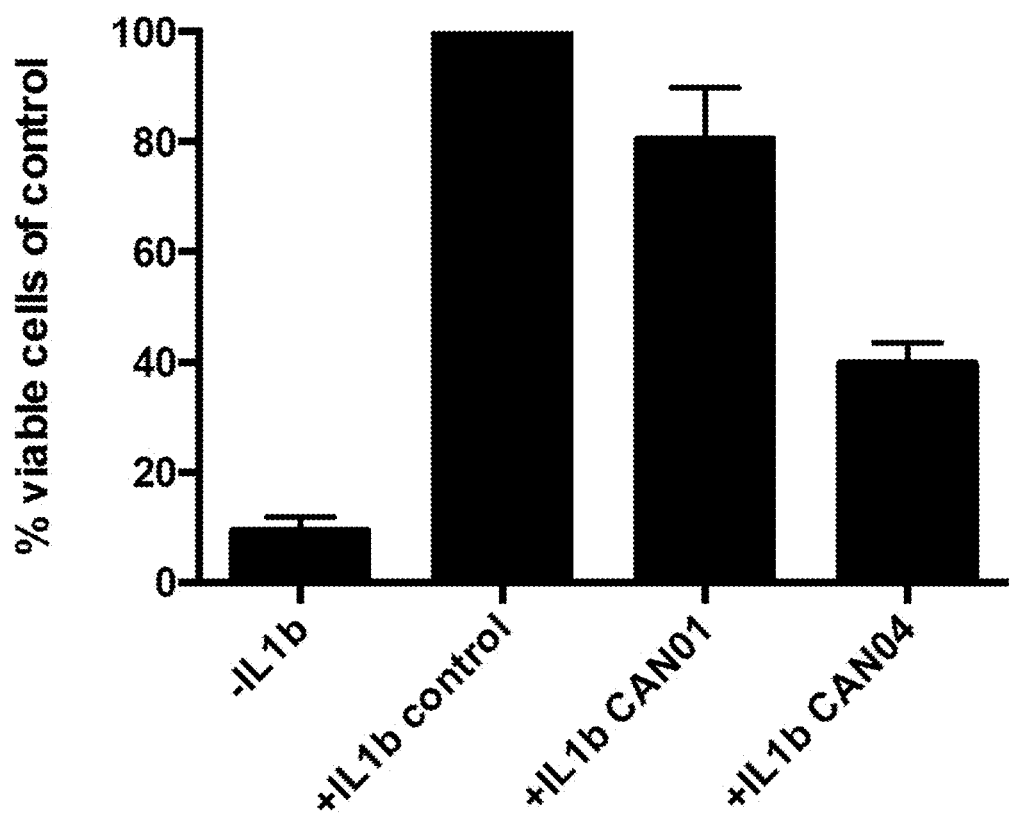

FIG. 5. The total cell expansion of primary primitive CML cells in presence of IL1b is significantly reduced with exemplary antibody CAN04 in comparison with both control and a reference antibody. The graph shows the combined result from three individual patient samples normalised to the control consisting of culturing without antibody or with isotype control antibody.

FIGS. 6A-D. In vitro ADCC assay shows that exemplary antibody CAN04 induces specific cell killing of CML cells. (6A) KU812, LAMA84, and BV173 cells were specifically killed by addition of 0.1 μg/mL CAN04. (6B) The cell killing mediated by exemplary antibody CAN04 is dose dependant as shown on BV173 target cells. (6C) Cell killing of primary cells from two CML blast crisis patients was induced by 1 μg/mL CAN04. (6D) Cells from a third CML blast crisis patient carrying the T3151 mutation were sensitive to the ADCC effect mediated by CAN04. Each experiment was performed at least twice with NK cells from different donors, and the presented data shows one representative experiment from each.

Figure 7:
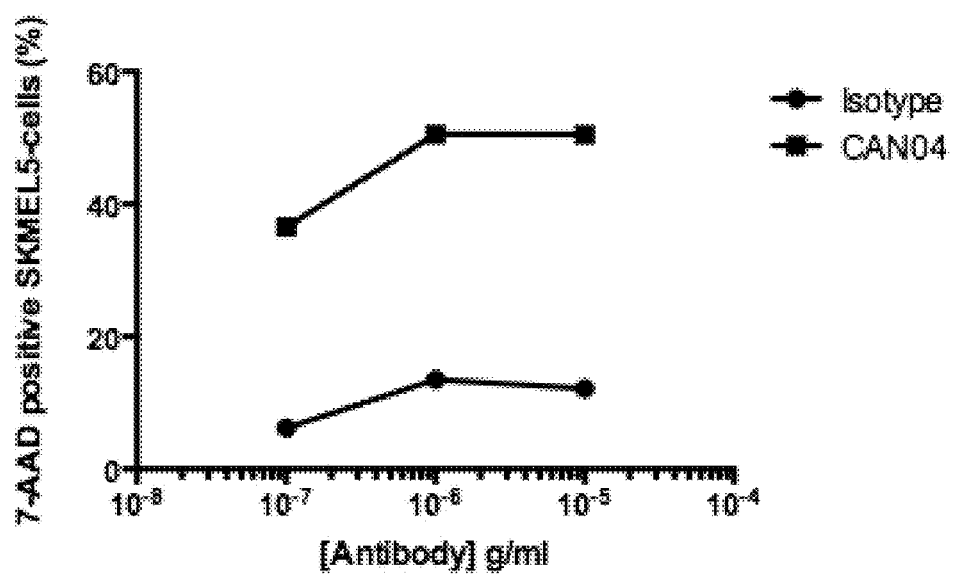

FIG. 7. In vitro ADCC assay showing that the exemplary CAN04 antibody is efficient in inducing specific cell killing of melanoma cells (SKMEL5 cell line). At all concentrations tested, as low as 0.1 µg/mL CAN04 shows a high specific killing. The experiment was performed at least twice with NK cells from different donors, and the presented data shows one representative experiment.

Figure 8A:
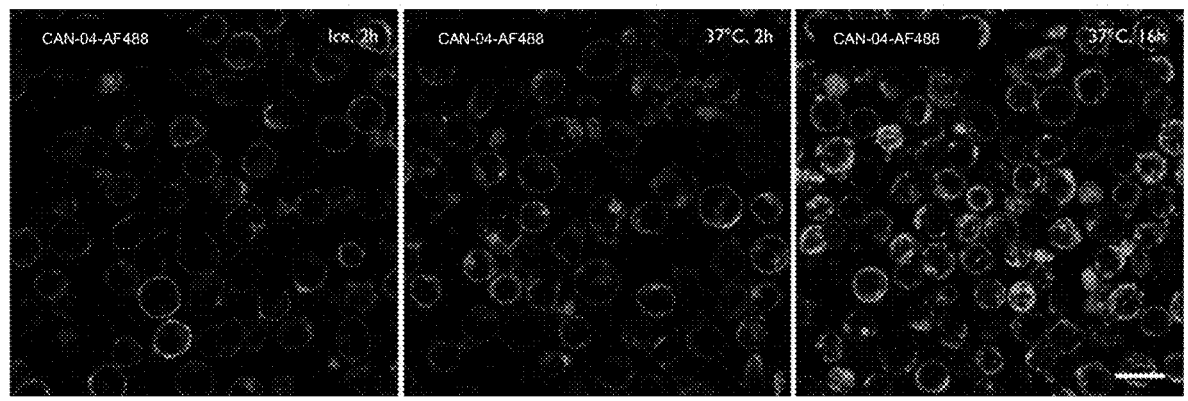
Figure 8B:
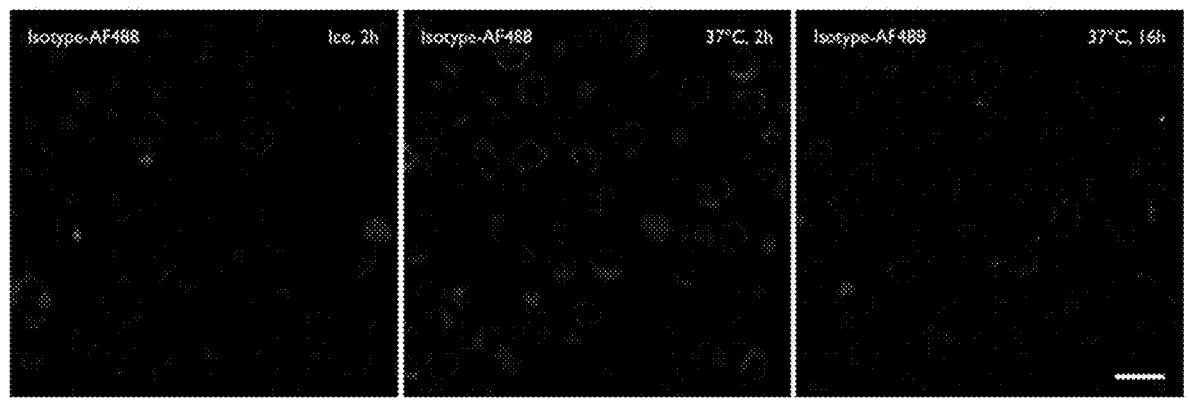

FIGS. 8A-B. (8A) Confocal images (one optical section, about 0.9 µm thick) showing LAMA cells incubated for 2 hours with CAN04-AF488 conjugated antibodies (green) on ice, or at 37° C. for 2 hours, or been incubated with CAN04-AF488 conjugated antibodies (green) for 16 hours at 37° C. A clearly defined antibody binding to the cell membrane of the majority of cells can be observed after 2 hours incubation on ice ("Ice 2h"). After incubation for 2 hours with CAN04-AF488 conjugated antibodies (green) at 37° C., in addition to membrane binding, antibodies have started to enter the cells (internalization) and are now localized also in the cytosol. After 16 hours of incubation at 37° C., the cell membrane binding is still present and the antibody internalization has produced accumulation of CAN04-AF488 antibodies in the majority of cells. Scale bar (right image) represents 20 µm in all images. (8B) Control for the CAN04-specific binding and internalization: The confocal images (one optical section, about 0.9 µm thick) show LAMA cells incubated with AF488 conjugated isotype control antibody on ice or at 37° C. for 2 hours, or at 37° C. for 16 hours. The isotype control antibody showed no specific binding at any of these conditions. Minor binding to cellular debris and necrotic cells (weak green) was noted. Scale bar (right image) represents 20 µm in all images.

FIGS. 9A-D. Treatment with CAN04 significantly reduces the leukemia burden. (9A) The frequency of leukemic cells in peripheral blood was lower in mice treated with exemplary antibody CAN04 compared to isotype control at day 36 after transplantation (1.2% vs. 22.7%, p<0.0001). (9B) The platelet (PLT) count remained at normal levels with CAN04 (p=0.0001). (9C) At time of sacrifice the frequency of leukemic cells in the bone marrow was reduced with CAN04 (38.7% vs. 91.5%; p<0.0001). (9D) The frequency of leukemic cells in spleen was lower in mice treated with CAN04 compared to isotype control (27.6% vs. 70.4%; p=0.0063).

Figure 10A:
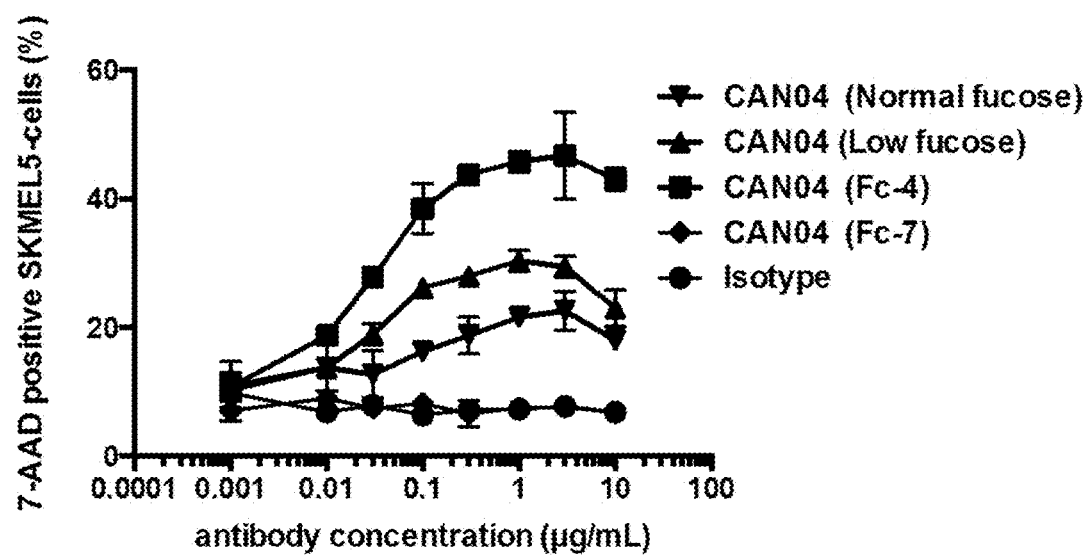
Figure 10B:
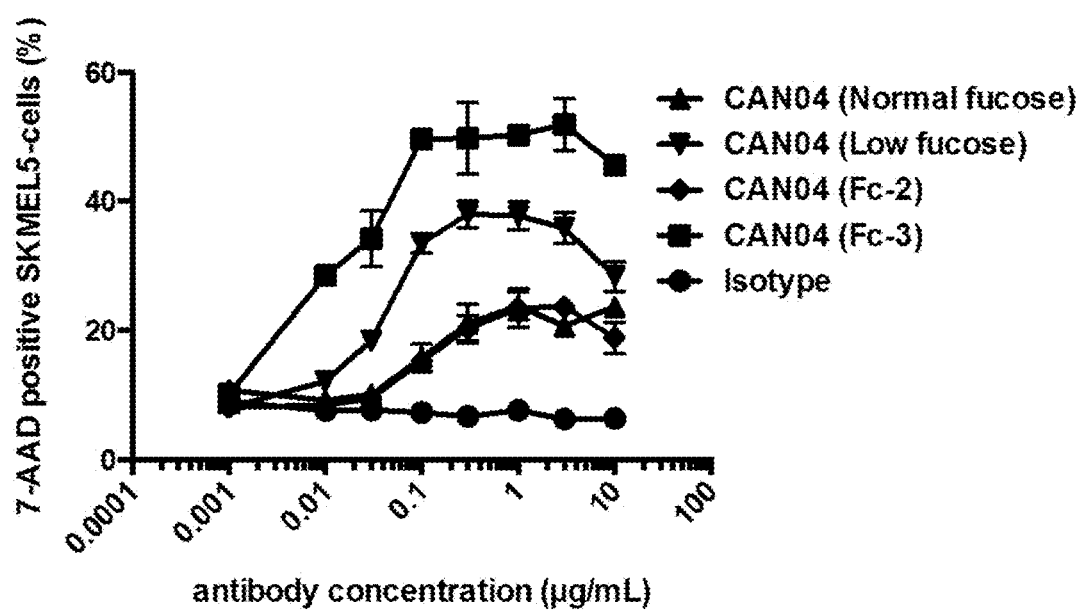
Figure 10C:
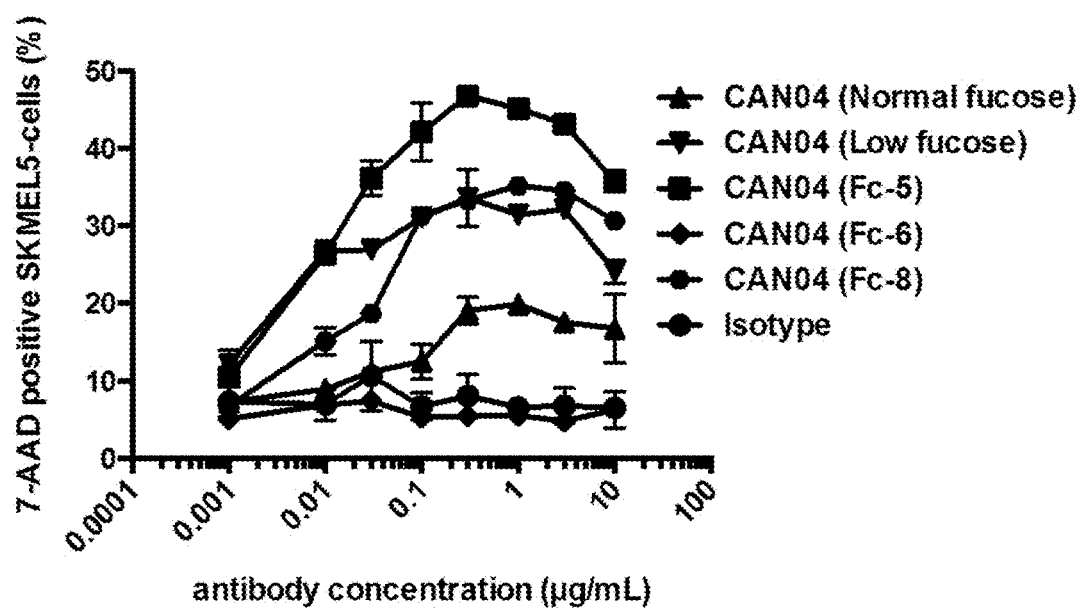

FIGS. 10A-C. The effect of low fucose and Fc mutations on ADCC activity, as determined using SKMEL5 cells. (10A) ADCC activity in SKMEL-5 of CAN04 (Fc-1) normal fucose, CAN04 (Fc-1) low fucose, Fc-4 and Fc-7. (10B) ADCC activity in SKMEL-5 of CAN04 (Fc-1) normal fucose, CAN04 (Fc-1) low fucose, Fc-2 and Fc-3. (10C) ADCC activity in SKMEL-5 of CAN04 (Fc-1) normal fucose, CAN04 (Fc-1) low fucose, Fc-5, Fc-6 and Fc-8.

EXAMPLES

A. Binding Affinity of Exemplary Antibodies of the Invention for IL1-RAP Protein
(i) Biacore Study—Anti-IL1RAP Antibodies of Murine Origin
Materials & Methods
Goat anti-mouse IgG was immobilized on a CM5 chip according to the technical manual of capture kit and standard operation principle of BIAcore T200 (Biacore Life Sciences, GE Healthcare Europe GmbH, Uppsala, Sweden).

The binding analysis cycle consisted of three steps: (i) capture of the ligand on the chip surface by immobilized anti-mouse antibody; (ii) binding of the analyte to the captured ligand; and (iii) dissociation of bound analyte.

The capture molecule surface was regenerated after each binding cycle using the manufacturer's recommended conditions.

All binding cycles were run at 25° C.

After five cycles of start-up, each antibody (100 nM) was injected at a flow rate of 30 µl/min, for 120 s, at the start of the cycle; then the analyte (100 nM) was injected at a flow rate of 30 µl/min, for 120 s, followed by monitoring the dissociation phase for 300 s.

One exemplary antibody of the invention (CAN04) was tested along with two comparator anti-IL1RAP antibodies (CAN01 and CAN03).
Results & Conclusions
Results are shown in Table 2 below:

TABLE 2

| Measurement of $K_{on}$, $K_{off}$ and $K_D$ | | | |
|---|---|---|---|
| Antibody | ka (1/M · s) | kd (1/s) | KD (M) |
| CAN01 | 2.34E+05 | 3.35E−04 | 1.43E−09 |
| CAN03 | 2.26E+05 | 7.25E−05 | 3.21E−10 |
| CAN04 | 4.27E+05 | 4.72E−05 | 1.10E−10 |

The exemplary antibody of the invention, CAN04, exhibited the highest affinity for human IL1RAP.
(ii) ELISA Study—Anti-IL1RAP Antibodies of Murine Origin
Materials & Methods
An indirect ELISA assay was performed. All samples were analysed in duplicate. Nunc-MaxiSorp 96 Micro Well™ Plates were coated with 100 ng of recombinant hIL1RAP 21-367 (100 µl/well) diluted in 0.01M PBS, pH 7.4, and incubated overnight at 4° C. Plates were washed with ELISA washing buffer (0.01M PBS, 0.05% Tween 20, pH 7.4) followed by a blocking step using 150 µl/well of ELISA blocking solution (PBS, 0.5% BSA, 0.05% Tween 20, pH 7.4). After 1 h incubation at room temperature (RT) on agitation the plates were washed again using ELISA washing buffer. Samples were diluted in three fold serial dilution (ranging from 1000 ng/ml to 0.5 ng/ml) in ELISA blocking solution and then transferred to the ELISA plate, 100 µl/well. Plates were incubated at RT for 1 h on agitation and then washed with ELISA washing solution. 100 µl/well of rabbit anti-mouse IgG conjugated to Alkaline Phosohatase (DAKO, 1:1000) was added and incubated 1 hour at RT on agitation. The plates were washed followed by addition of substrate (4-Nitrophenyl phosphatise disodium salt hexahydrate, SIGMA, 1 mg/ml), 100 µl/well. The plates were thereafter incubated at RT on agitation and absorbance at 405 nm measured consecutively for 30 min. Absorbance at 0 min was taken as background signal.
Results & Conclusions
Results are shown in FIG. 1
The exemplary antibody of the invention, CAN04, was found to possess the highest binding signal for human IL1RAP.
(iii) ELISA Study—Humanised Versions of the Exemplary 'CAN04' Antibody Materials & Methods Heavy and light chain variable domains of sixteen humanised variants of CAN04 (hCAN04) were sub-cloned into vectors containing human constant domains:
Kappa constant domain for VL domain [SEQ ID NO:18]
IgG1za heavy chain constant for VH domain [SEQ ID NO:19]

Antibodies were transiently expressed in CHOK1SV cells in a volume of 200 ml (shaker flask).

Antibodies were purified using Protein A affinity chromatography.

Purified antibodies were analysed by SDS-PAGE and SE-HPLC.

An indirect ELISA assay was performed as described above with the alteration that the samples were diluted in a three-fold serial dilution starting at 3.5 nM and run in replicates of four.

Results & Conclusions

Results are shown in Table 3.

TABLE 3

Affinity for hIL1RAP as determined by ELISA

| Antibody | Heavy chain* | Light Chain** | $K_D$ (pM) |
| --- | --- | --- | --- |
| CAN04 (murine) | SEQ ID NO: 1 | SEQ ID NO: 2 | 88 ± 2 |
| hCAN04 Variant 1 | SEQ ID NO: 8 | SEQ ID NO: 15 | 125 ± 2 |
| hCAN04 Variant 2 | SEQ ID NO: 9 | SEQ ID NO: 15 | 171 ± 4 |
| hCAN04 Variant 3 | SEQ ID NO: 10 | SEQ ID NO: 15 | 450 ± 68 |
| hCAN04 Variant 4 | SEQ ID NO: 11 | SEQ ID NO: 15 | 470 ± 50 |
| hCAN04 Variant 5 | SEQ ID NO: 8 | SEQ ID NO: 16 | 135 ± 2 |
| hCAN04 Variant 6 | SEQ ID NO: 9 | SEQ ID NO: 16 | 173 ± 4 |
| hCAN04 Variant 7 | SEQ ID NO: 10 | SEQ ID NO: 16 | 526 ± 44 |
| hCAN04 Variant 8 | SEQ ID NO: 11 | SEQ ID NO: 16 | 402 ± 64 |
| hCAN04 Variant 9 | SEQ ID NO: 8 | SEQ ID NO: 17 | 210 ± 4 |
| hCAN04 Variant 10 | SEQ ID NO: 9 | SEQ ID NO: 17 | 301 ± 5 |
| hCAN04 Variant 11 | SEQ ID NO: 10 | SEQ ID NO: 17 | 504 ± 26 |
| hCAN04 Variant 12 | SEQ ID NO: 11 | SEQ ID NO: 17 | 620 ± 68 |

*The heavy chain also comprised the IgG1za heavy chain constant domains [SEQ ID NO: 19].
**The light chain also comprised a kappa constant domain [SEQ ID NO: 18].

Four of the sixteen humanised versions of CAN04 showed minimal or no binding to IL1RAP (data not shown).

B. Binding of Exemplary Antibodies of the Invention to IL1RAP-Expressing Cells (i) Flow Cytometry Study—Anti-IL1RAP Antibodies of Murine Origin Materials & Methods Chronic myeloid leukemia (CML) cell line KU812 cells were stained with antibodies raised against IL1RAP or a relevant isotype control. For detection, a secondary anti-mIg-APC was used.

One exemplary antibody of the invention (CAN04) was tested along with seven comparator anti-IL1RAP antibodies (CAN01, CAN02, CAN03, CAN05, CAN07, CAN08 and CAN09). An isotype negative control antibody was also included.

For analysis of primary leukemic cells, three CD34-enriched CML patient samples and five acute myeloid leukemia (AML) patient samples enriched for mononuclear cells were stained with CAN04-PE at concentrations of 1 µg/mL and 5 µg/mL respectively, or a PE-conjugated isotype control. Cells were analysed using a FACS CANTO flow cytometer (BD).

Results & Conclusions

Staining of IL1RAP-expressing KU812 leukemia cells reveals a higher mean fluorescence intensity (MFI) for CAN04 compared to the isotype control and other comparator antibodies targeting IL1RAP (FIG. 2 A). Labelling of primary cells from five AML and three CML patients using CAN04 result in staining above the isotype control in flow cytometric analysis (FIG. 2 B-C). The present study shows that CAN04 specifically bind IL1RAP with a higher MFI than other tested monoclonal antibodies on a CML cell line, and that CAN04 also bind to primary CML and AML cells.

(ii) Flow Cytometry Study—Humanised Versions of 'CAN04' Antibody

Materials & Methods

Chronic myeloid leukemia (CML) cell line BV173 cells were stained with 1 µg/mL test antibody or a relevant isotype control. For detection, a secondary anti-hIgG-PE was used. Cells were analysed using a FACS CANTO flow cytometer (BD).

The test antibodies included one chimeric anti-IL1RAP antibody ('chimary') and twelve different humanised versions of the exemplary CAN04 antibody of the invention ('Var1' to 'Var 12').

Results & Conclusions

Staining of IL1RAP-expressing BV173 leukemia cells shows that the humanised CAN04 variants stain with different intensity, but all at levels above the isotype control (see FIG. 3). Humanized variants 1, 2, 5, 6, 9 and 10 of CAN04 (see Table 3) exhibit the strongest labelling.

C. Epitope/Domain Mapping of Exemplary Antibodies of the Invention

Materials & Methods

In order to understand where the different antibody clones bind on the IL1RAP, a structural analysis of the protein was performed revealing that the extracellular part of the receptor could be divided into three distinct domains hereafter referred to as domains 1, 2 and 3 (D1, D2, D3) (see Wang et al., 2010, Nature Immunology, 11:905-912, the disclosures of which are incorporated herein by reference). In order to determine the domain-binding pattern for the different antibody clones, a series of receptor constructs were generated and binding to these tested in an ELISA assay.

An indirect ELISA assay was performed. All samples were analysed in duplicate. Nunc-MaxiSorp 96 Micro Well™ Plates were coated with 100 ng of Rec hIL1 RAP Domain123 (aa21-367) (positive control), Rec hIL1RAP Domain12 (aa21-234), Domain1 (aa21-134) or Rec hIL1RAP Domain3 (aa235-367) (100 µl/well) diluted in 0.01M PBS, pH 7.4, and incubated overnight at 4° C. Plates were washed with ELISA washing buffer (0.01M PBS, 0.05% Tween 20, pH 7.4) followed by a blocking step using 150 µl/well of ELISA blocking solution (PBS, 0.5% BSA, 0.05% Tween 20, pH 7.4). After 1 h incubation at room temperature (RT) on agitation the plates were washed again using ELISA washing buffer. CAN01, CAN03, CAN04, CAN05, CAN07, CAN08 and KMT-1 (positive control) were diluted in three fold serial dilution (ranging from 1000 ng/ml to 0.5 ng/ml) in ELISA blocking solution and then transferred to the ELISA plate, 100 µl/well. Plates were incubated at RT for 1 h on agitation and then washed with ELISA washing solution. 100 µl/well of rabbit anti-mouse IgG conjugated to Alkaline Phosphatase (DAKO, 1:1000) was added and incubated 1 hour at RT on agitation. The plates were washed followed by addition of substrate (4-Nitrophenyl phosphatise disodium salt hexahydrate, SIGMA, 1 mg/ml), 100 l/well. The plates were thereafter incubated at RT on agitation and absorbance at 405 nm measured consecutively for 30 min. Absorbance at 0 min was taken as background signal.

One exemplary antibody of the invention (CAN04) was tested along with nine comparator anti-IL1RAP monoclonal antibodies (CAN01, CAN02, CAN03, CAN05, CAN07, CAN08, CAN10, and CAN11, together with a polyclonal anti-IL1RAP antibody (KMT-1) as a positive control.

Results & Conclusions

A majority of anti-IL1RAP antibodies tested for target validation bind to domain 3 (D3). However, the exemplary CAN04 antibody of the invention is distinct in that it binds to domain 2 (D2). The entire domain mapping data can be found summarized in the Table 4 below.

TABLE 4

Epitope mapping of exemplary anti-IL1RAP antibody clones.

| Clone | Domain123 (ac/21-367) | Domain12 (aa21-234) | Domain1 (ac/21-134) | Domain3 (ac/235-367) | Suggested epitope |
|---|---|---|---|---|---|
| CAN03 | + | | | + | D3 |
| CAN05 | + | + | + | | D1 |
| CAN07 | + | | | + | D3 |
| CAN08 | + | | | + | D3 |
| CAN04 | + | + | | | D2 |
| CAN01 | + | | | + | D3 |
| CAN02 | + | | | | nd* |
| KMT-1 | + | + | + | + | polyclonal | nd* = not determined as epitope mapping data could not clearly identify specific domain for these constructs, which may be attributed to binding to a structural epitope containing sequence elements from more than one domain, e.g. D2-D3 junction.

D. Specificity/Cross-Reactivity of Exemplary Antibodies of the Invention

Materials & Methods

An important feature of a good lead candidate antibody is that it cross-reacts with equal or near-equal potency to the homologous protein in a relevant toxicology species. According to the general regulatory guidelines, binding to one rodent and one non-rodent would be the preferred scenario, but for antibodies this is rarely the case, and instead many labs struggle to identify any relevant toxicology species except for primates.

For the present study, cross reactivity to non-human primates like *Macaca mulatta* (rhesus) or *Macaca fascicularis* (cynomolgus) was expected since the IL1RAP protein in these species share 99% homology to the human IL1RAP protein.

A number of potential lead antibodies were selected and tested for binding to recombinant *M. fascicularis* IL1RAP (aa21-367) in an ELISA assay.

One exemplary antibody of the invention (CAN04) was tested along with eight comparator anti-IL1RAP monoclonal antibodies (CAN01, CAN02, CAN03, CAN07, CAN08, CAN09, Mab676 from R&D, and a polyclonal anti-IL1RAP antibody (KMT-1).

Results & Conclusions

Surprisingly, several of the comparator anti-L1 RAP antibodies tested were found not to cross-react with cynomolgus IL1RAP, amongst them the commercial reference antibody mAb676 from R&D, Table 5.

TABLE 5

Binding to cynomolgus IL1RAP
(Values in bold denotes clones identified to cross-react with IL1RAP from *M. fascicularis*)

| Clone | Binding to rec. *M. fascicularis* IL1RAP ($OD_{405}$) |
|---|---|
| CAN01 | 0.324 |
| CAN02 | 0.014 |
| CAN09 | 0.022 |

TABLE 5-continued

Binding to cynomolgus IL1RAP
(Values in bold denotes clones identified to cross-react with IL1RAP from *M. fascicularis*)

| Clone | Binding to rec. *M. fascicularis* IL1RAP ($OD_{405}$) |
|---|---|
| CAN03 | 0.870 |
| CAN04 | 0.416 |
| CAN07 | 0.111 |
| CAN08 | 0.375 |
| mAb676 (R&D) | 0.037 |
| KMT-1 | 0.481 |

E. Inhibition of IL-1α, IL-1β and IL-33 Signalling by Exemplary Antibodies of the Invention (i) Effect of CAN04 on IL-1 Signalling in HEK-Blue IL-33/IL-1β Cell Line Materials & Methods As IL1RAP is a functional part of the IL-1 receptor complex, antibodies binding to IL1RAP may also inhibit IL-1 signalling. Since a number of tumour cell types have been shown to use IL-1 as a growth factor, this may be an important additional mechanism for mediating anti-tumour effects.

In order to test for the capability of potential lead candidate antibodies to block IL-1 signalling, an IL-1 dependent reporter gene assay was set up. HEK-Blue IL-33/IL-13 cells (InvivoGen) respond to IL-1 signalling by the release of alkaline phosphatase that can be quantified by a colorimetric assay. To test the inhibitory capacity of the lead candidates HEK-Blue cells were plated at 50 000 cells/well and incubated with the test antibodies 45 minutes prior to stimulation with IL-1α, IL-1β or IL-33 in a final concentration in assay of 0.3 ng/ml for each ligand. Final assay concentrations of antibodies were 100 nM-0.01 nM. In the control wells, the antibodies were replaced by PBS. The cells were incubated at 37° C. o/n before measuring the amount of alkaline phosphatase released. Antibodies were also tested for potential agonistic effects by incubating the cells in the presence of a high concentration of antibody (10 mg/ml) in the absence of additional stimuli. Any IL-1R agonistic effects would thus be recorded as a release of alkaline phosphatase.

One exemplary antibody of the invention (CAN04) was tested along with two comparator anti-IL1RAP monoclonal antibodies (CAN01 and CAN 03) and an isotype negative control antibody.

Results & Conclusions

As depicted in FIG. 4(A), the exemplary antibody CAN04 induced a pronounced inhibition of IL-1β signalling. Comparator antibody CAN03 also produced a detectable inhibition but significantly less than CAN04. Neither the comparator CAN01 nor the isotype control produced any measurable inhibition of IL1 signalling.

In addition to blocking IL-1β, CAN04 is also a potent inhibitor of IL-1α and IL-33 signalling; see FIGS. 4(B) and (C), respectively.

None of the tested candidates showed any agonistic effect.

(ii) Effect in Primary CML Cells

Materials & Methods

Bone marrow aspirates or peripheral blood was drawn from three patients with chronic myeloid leukemia (CML) in chronic phase. Mononuclear cells were isolated by centrifugation over Lymphoprep, and samples were enriched for CD34+ cells using an anti-CD34 antibody and magnetic beads (Miltenyi biotech.) The CD34+ cells were kept in liquid nitrogen until use, when they were thawed and stained with antibodies against CD34 and CD38. Propidium iodide was used as viability marker. Using a FACS Aria cell sorter, viable CD34+CD38− cells were sorted at a density of 2500 cells per well into 96 wells tissue culture treated plates containing 100 μl serum free Stemspan culturing medium without supplements. After sorting, IL1b and the test antibody were added to the wells in a total of 100 ul Stemspan to produce a final volume of 200 μl per well with 0-0.4 ng/mL IL1b and 0-10 μg/mL antibody. The plates were incubated at 37° C., 5% $CO_2$, for 7 days after which the number of viable (7AAD−) cells were counted using Countbright counting beads and a FACS Canto.

One exemplary antibody of the invention (CAN04) was tested along with one comparator anti-IL1RAP monoclonal antibodies (CAN01) and an isotype negative control antibody.

Results & Conclusions

As shown in FIG. 5, culturing of CD34+CD38− primary chronic phase CML cells in the presence of IL1b results in increased cell expansion. The IL1-induced increase in cell expansion is significantly reduced upon addition of the exemplary CAN04 antibody to the culture (p<0.0001). Also in comparison with another IL1RAP-targeting antibody, CAN01, CAN04 is significantly more effective in reducing the total cell expansion (p=0.0022). We conclude that binding of CAN04 to IL1RAP interferes with the stimulation in cellular expansion induced by IL1 in primary primitive CML cells.

F. ADCC Effect of Exemplary Antibodies of the Invention
(i) Chronic Myeloid Leukemia (CML) Cell Lines
Materials & Methods Chronic myeloid leukemia (CML) cell lines KU812, LAMA84 and BV173, or primary cells from three patients with CML in blast crisis were used as target cells in the in vitro antibody dependent cellular cytotoxicity (ADCC) assay. Briefly, target cells were labelled with PKH26 (Sigma-Aldrich, St Louis, Mo.) according to manufacturer's instructions, and seeded into a 96-well plate at a density of 5,000-10,000 cells per well. Subsequently, the exemplar antibody of the invention, CAN04, or isotype control antibody was added to wells in different concentrations and incubated for 30 min before 100,000 NK effector cells were added to each well. NK-cells were extracted from healthy volunteers after informed consent by using an NK-cell negative cell isolation kit according to manufacturer's instructions (Miltenyi Biotech, Bergisch Gladbach, Germany). A non-specific human IgG1 antibody was used as an isotype negative control in the experiments (Eureka Therapeutics, Emeryville, Calif.). The degree of cell death was assessed by detection of 7-AAD positive cells using a FACS CANTO flow cytometer (BD). Each experiment was performed at least twice with NK cells from different donors.

Results & Conclusions

Figure 6A:
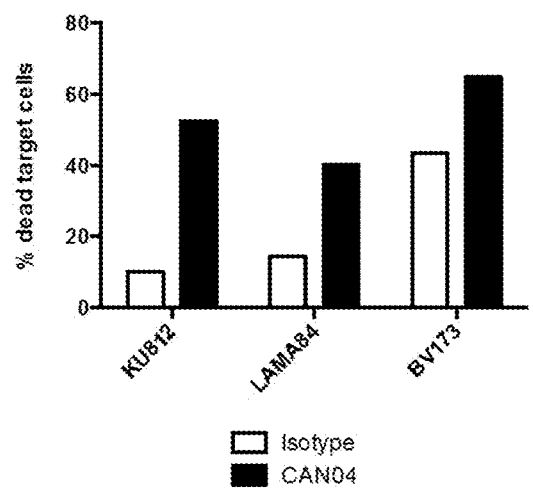
Figure 6B:
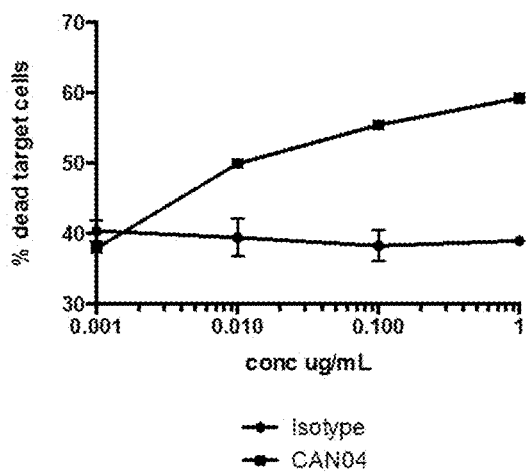
Figure 6C:
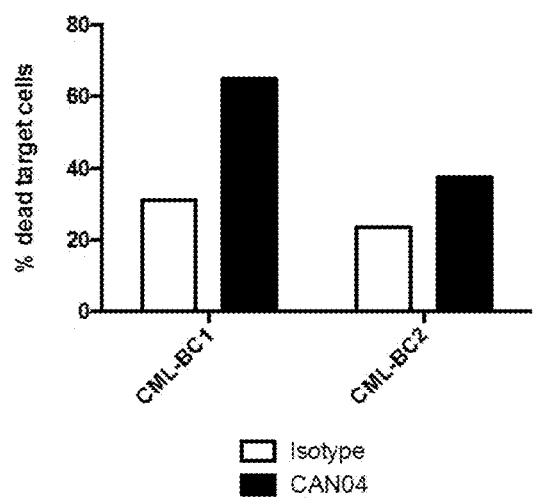
Figure 6D:
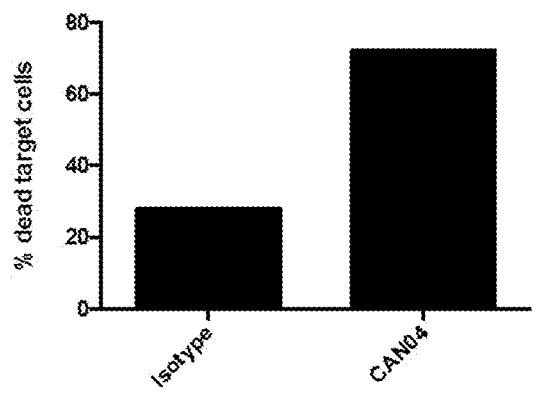

The in vitro ADCC assay shows that the exemplary antibody of the invention, CAN04, directs NK-cells to kill CML cell lines KU812, LAMA84 and BV173 to a higher degree than the isotype control (FIG. 6A). A dose titration of CAN04 using BV173 target cells shows that the effect on cell killing is dose dependent with a higher degree of cell killing with increasing CAN04 concentration (FIG. 6B). Chronic myeloid leukemia that has progressed into blast crisis display only transient effect to treatment with tyrosine kinase inhibitors and thus imposes a major treatment problem. The ADCC assay with primary cells from two individual CML blast crisis patients shows that these cells were sensitive to the cellular cytotoxicity induced by CAN04 and NK-cells (FIG. 6C). In addition, primary cells from a third CML blast crisis patient harbouring the T3151 mutation that cause resistance to several tyrosine kinase inhibitors display similar sensitivity (FIG. 6D). Altogether, the experiments show that CAN04 has the ability to direct NK-cells to specific cell killing of CML cell lines as well as primary blast crisis CML cells, and that the cytotoxic effect induced by CAN04 is dose dependent.

(ii) Melanoma Cell Lines
Materials & Methods

The malign melanoma cell line SKMEL-5 was used as a target for in vitro antibody dependent cellular cytotoxicity (ADCC) assay. Briefly, target cells were labelled with PKH26 (Sigma-Aldrich, St Louis, Mo.) according to manufacturer's instructions, and seeded into a 96-well plate at a density of 5,000-10,000 cells per well. Subsequently, CAN04 or isotype control antibody were added to wells in different concentrations and incubated for 30 min before 100,000 NK effector cells were added to each well. NK-cells were extracted from healthy volunteers after informed consent by using an NK-cell negative cell isolation kit according to manufacturer's instructions (Miltenyi Biotech, Bergisch Gladbach, Germany). A non-specific human IgG1 antibody was used as control in the experiments (Eureka Therapeutics, Emeryville, Calif.). The degree of cell death was assessed by detection of 7-AAD positive cells using a FACS CANTO flow cytometer (BD). Each experiment was performed at least twice with NK cells from different donors.

Results & Conclusions

The in vitro ADCC assay showed that CAN04 directs NK-cells to killing of the SKMEL-5 cell line to a much higher degree than a matching isotype control (FIG. 7). The dose titration of CAN04 showed that CAN04 is efficient in inducing ADCC, at low concentrations (FIG. 7). In summary, these data demonstrate that CAN04 has the ability to direct NK-cells to specific cell killing of SKMEL-5 in a dose dependent manner and that CAN04.

G. Internalisation of Exemplary Antibodies of the Invention
Materials & Methods

Cells and Culture Conditions: LAMA-84 cells, a cell-line established from a patient with chronic myeloid leukemia in blast crisis, were obtained from DSMZ (Braunschweig, Germany) and cultured according to the recommendation by the supplier. Briefly, cells were cultured in RPMI 1640 with 10% FBS, 1% Glutamine and 1% Penicillin/Streptomycin in 5% $CO_2$, 37° C. Cell cultures were split to a density of $0.5 \times 10^6$ cells/ml every 2-3 days. Cells were used for up to 12 passages after they were received from DSMZ.

Cells from the suspension cell-line LAMA-84 were washed once in phosphate buffered saline (PBS) supplemented with 1% Bovine serum albumin (BSA) and resuspended in PBS-BSA supplemented with 5% human AB+ serum from Sigma and incubated for 5 minutes at room temperature (RT). The AlexaFluor488 (AF488) labelled IL-1RAP selective antibody CAN04, or isotype matched control antibody, was added to a final concentration of 10 μg/ml. Cells were placed (incubated) on ice or at 37° C. for 2 or 16 hours.

For the image analysis with confocal microscopy (LSM 510 Meta Zeiss confocal microscope), cells were washed twice in PBS-1% BSA, were briefly spun down followed by resuspension in 3% paraformaldehyde (in PBS) fixation for 20 minutes (at 4° C.). Cells were then spun down, resuspended in PBS containing 0.001% Triton X-100 (PBS-TX) and a nuclear marker (DAPI), and were let to incubate for 5 minutes at RT. After a brief centrifugation cells were resuspended in PBS-TX and placed in glass-bottomed microscope wells. Cells were then let to adhere for one hour. Image data were collected via confocal scanning of cells providing high-resolution images of AlexaFluor488 fluorescence in thin optical sections through the centre of cells (depicted by nuclear marker). Further analyses of antibody binding to cell membrane and/or internalized antibodies were performed via software image analyses (Zeiss Zen2010).

Results & Conclusions

The structural relation of CAN04 binding to the cell membrane and its capacity to enter the cells ("internalize") was demonstrated with high resolution imaging data recorded by means of confocal laser scanning microscopy, and by image analyses of this data.

Image data representations are shown in FIG. 8.

H. Therapeutic Efficacy In Vivo of an Exemplary Antibody of the Invention

Materials & Methods

Unconditioned NOD/SCID mice were engrafted with lethal doses of MA9Ras cells, previously generated by transformation of human umbilical cord blood CD34$^+$ cells by retroviral integration of cDNAs directing the expression of an MLL/AF9 fusion and an activated NRAS gene. Leukemic mice were treated with the exemplary CAN04 antibody targeting IL1RAP, or a corresponding isotype control antibody. The antibodies were administered by intraperitoneal injections twice weekly throughout the experiment with first treatment given day three after transplantation. Each dose of antibody was 500 μg, except for the first that was given as a bolus of 1000 μg. Mice were sacrificed upon signs of severe disease as judged by hunchback, untidy fur, and decreased mobility, or due to solid tumours.

Results & Conclusions

Figure 9A:
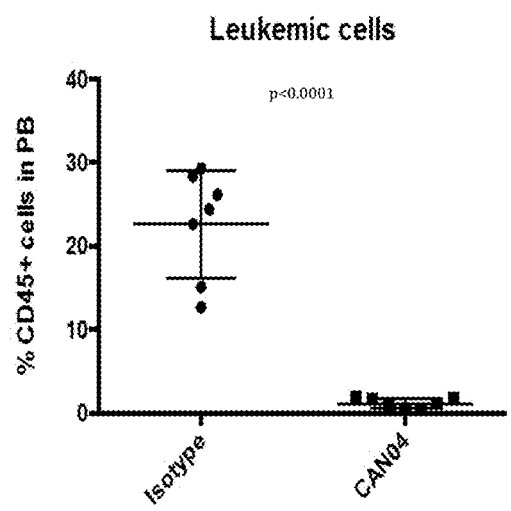
Figure 9B:
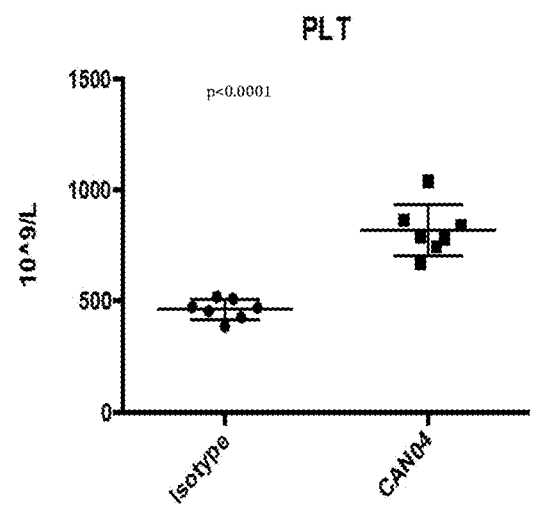
Figure 9C:
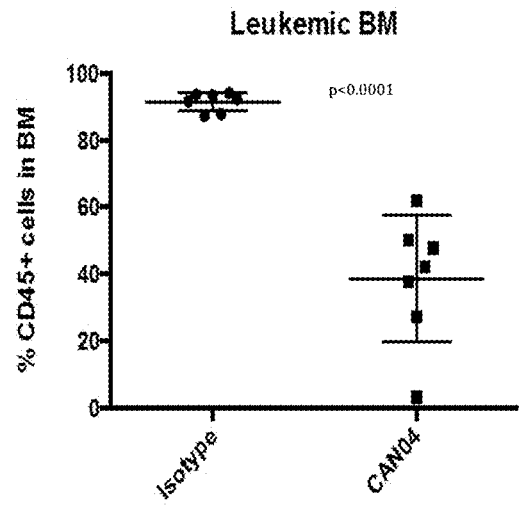
Figure 9D:
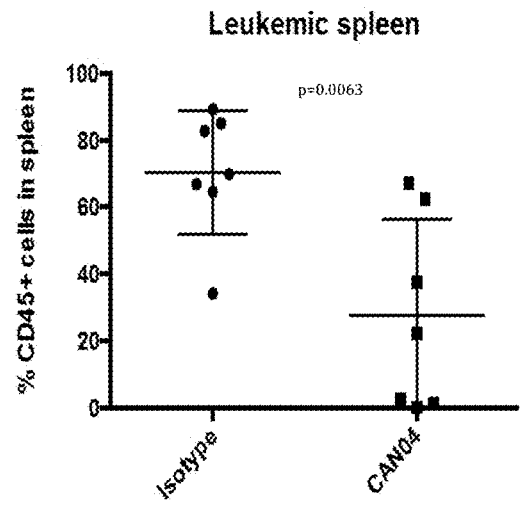

Immunodeficient mice were engrafted with human leukemic cells and treated with CAN04, a monoclonal antibody targeting IL1RAP. The frequency of leukemic cells in peripheral blood was significantly reduced at day 36 after transplantation, and the platelet counts remained normal in mice given CAN04compared to isotype control antibody indicating a more functional haematopoiesis (FIG. 9A-B). CAN04 treatment resulted in a significant reduction of leukemic cells in bone marrow and spleen (FIG. 9C-D). We conclude that anti-IL1RAP immunotherapy reduces human leukemia in peripheral blood, bone marrow, and spleen, in the MA9Ras xenograft model. The results support anti-IL1RAP immunotherapy as a new promising therapeutic strategy for AML.

I. Effect of (a) Low Fucose Antibodies and (b) Fc Mutations on ADCC Activity

Materials & Methods

The humanised heavy chain variable domain variant of CAN04 (comprising SEQ ID No: 9) was sub-cloned into vector containing the of IgG1za human constant domain (SEQ ID NO:19). The humanised light chain variable domain variant of CAN04 (comprising SEQ ID No: 16) was sub-cloned into vector containing the Kappa human constant domain (SEQ ID NO:18).

To examine the effect of low fucose, hCAN04 antibody "Fc-1" (see below) were transiently expressed by co-transfection of the resulting vectors into HEK293 cells cultured in medium containing Kinfunensine. Antibody Fc-1, produced by expression in the absence of Kinfunensine, was used as the 'Normal Fucose' control To address how various Fc-engineered mutants of hCAN04 affect the ADCC activity, genetically engineered hCAN04 variants were generated as follows:

Fc-1=(Humanised CAN04 with wildtype Fc; i.e. hCAN04variant 6 in Table 3)
Fc-2=(As Fc-1 but with mutations S239D/S298A/I332E)
Fc-3=(As Fc-1 but with mutations S239D/A330L/I332E)
Fc-4=(As Fc-1 but with mutations S239D/I332E)
Fc-5=(As Fc-1 but with mutations S298A/E333A/K334A)
Fc-6=(As Fc-1 but with mutation N297Q)
Fc-7=(As Fc-1 but with mutation N297S)
Fc-8=(As Fc-1 but with mutations P247I/A339Q)

wherein the position of the amino acid mutations is defined using the Eu Numbering Scheme, which differs from the numbering in SEQ ID NOS: 18 and 19 above; see Edelman et al., 1969, *Proc. Natl. Acad. Sci. USA*, 63:78-85).

Antibodies were purified using Protein A affinity chromatography.

ADCC assays were performed using the SKMEL5 cell line.

Results & Conclusions

A low fucose variant of hCAN04, produced in the presence of kinfunensine, was superior to a normal fucose CAN04-variant (FIG. 10).

The effect of Fc mutation on ADCC activity was dependent upon the mutation(s) made. Thus:

(a) ADCC-activity of the Fc-6 and Fc-7 variants of humanised CAN04 was completely abrogated;
(b) ADCC-activity of the Fc-3, Fc-4, and Fc-5 variants of humanised CAN04 was enhanced, even relative to the low fucose variant of CAN04;
(c) ADCC-activity of the Fc-8 variant of humanised CAN04 was similar to that of the low fucose form of CAN04
(d) ADCC-activity of the Fc-2 variant of humanised CAN04 was similar to that of the normal fucose form of CAN04.

Example J—Analysis of Competitive Binding by ELISA

Protocol

All samples should be analysed in duplicate.

Coat a Nunc-MaxiSorp 96 Micro Well™ Plate with 100 ul/well of recombinant hIL1RAP 21-367 (1 ug/ml) diluted in 0.01M PBS, pH 7.4.

Incubate the plate overnight at 4° C.

Wash the plate with ELISA washing buffer (0.01M PBS, 0.05% Tween 20, pH 7.4).

Add 150 μl/well of ELISA blocking solution (PBS, 0.5% BSA, 0.05% Tween 20, pH 7.4).

Incubate the plate for 1 h at room temperature (RT) under agitation.

Wash the plate with ELISA washing buffer.

Add samples of test items (e.g. mAb 1, mAb 2) to wells (100 ul/well, 10 ug/ml)

Incubate the plate for 1 h at RT.

Wash the plate with ELISA washing solution.

Add a solution of reference antibody CAN04 (100 ul/well, 1 ug/ml) to all wells.

Incubate the plate for 1 h at RT.

Wash the plate with ELISA washing buffer.

Add 100 μl/well of a suitable secondary antibody conjugated to Alkaline rabbit anti-mouse IgG conjugated to Alkaline Phosphatse (If the test items are human antibodies, a suitable secondary antibody would be Goat Anti-Mouse IgG (Fc specific)-Alkaline Phosphatase antibody, SIGMA, A1418)

Incubate the plate for 1 h at RT under agitation.

Wash the plate with washing buffer.

Add 100 μl of pNPP substrate per well.
(4-Nitrophenyl phosphatise disodium salt hexahydrate, SIGMA, 1 mg/ml).

Incubate the plate at RT under agitation and measure absorbance at 405 nm consecutively for 30 min. Absorbance at 0 min should be taken as background signal.

---

The invention claimed is:

1. A recombinant host cell comprising:
A) a nucleic acid molecule encoding an antibody or antigen-binding fragment thereof or a component polypeptide chain thereof; or
B) a vector comprising said nucleic acid molecule in A), wherein the antibody comprises:
a. A heavy chain variable region (VH) comprising (i) heavy chain CDR1 comprising: GYAFTSS (amino acids 26-32 of SEQ ID NO:9); (ii) Heavy chain CDR2 comprising: YPGDGN (SEQ ID NO: 4); and (iii) Heavy chain CDR3 comprising: GYLDPMDY (SEQ ID NO: 5); and a light chain variable region (VL) comprising: (i) Light chain CDR 1 comprising: ASQGINNYLN (amino acids 25-34 of SEQ ID NO:16); (ii) Light chain CDR2 comprising: YTSGLHA (SEQ ID NO: 13); and (iii) Light chain CDR3 comprising: QQYSILPWT (SEQ ID NO: 14);
b. A heavy chain variable region (VH) comprising (i) heavy chain CDR1 comprising GYAFTSS (amino acids 26-32 of SEQ ID NO:9); (ii) heavy chain CDR2 comprising YPGDGN (SEQ ID NO: 4); and (iii) heavy chain CDR3 comprising GYLDPMDY (SEQ ID NO: 5); and a light chain variable region (VL) comprising (i) light chain CDR 1 comprising SASQGINNYLN (SEQ ID NO:12); light chain CDR2 comprising YTSGLHA (SEQ ID NO: 13); and (iii) light chain CDR3 comprising QQYSILPWT (SEQ ID NO: 14);
c. A heavy chain variable region (VH) comprising (i) heavy chain CDR1 comprising GYAFSSS (SEQ ID NO:3); (ii) heavy chain CDR2 comprising YPGDGN (SEQ ID NO: 4); and (iii) heavy chain CDR3 comprising GYLDPMDY (SEQ ID NO: 5); and a light chain variable region (VL) comprising (i) light chain CDR 1 comprising SASQGINNYLN (SEQ ID NO:12); light chain CDR2 comprising YTSGLHA (SEQ ID NO: 13); and (iii) light chain CDR3 comprising QQYSILPWT (SEQ ID NO: 14);
d. A heavy chain variable region (VH) comprising (i) heavy chain CDR1 comprising GYAFSSS (SEQ ID NO:3); (ii) heavy chain CDR2 comprising YPGDGN (SEQ ID NO: 4); and (iii) heavy chain CDR3 comprising GYLDPMDY (SEQ ID NO: 5); and a light chain variable region (VL) comprising (i) light chain CDR 1 comprising ASQGINNYLN (amino acids 25-34 of SEQ ID NO:16); light chain CDR2 comprising YTSGLHA (SEQ ID NO: 13); and (iii) light chain CDR3 comprising QQYSILPWT (SEQ ID NO: 14);
e. A heavy chain variable region (VH) comprising (i) heavy chain CDR1 comprising GYTFTSS (amino acids 26-32 of SEQ ID NO:10); (ii) heavy chain CDR2 comprising YPGDGQ (amino acids 52-57 of SEQ ID NO:10); and (iii) heavy chain CDR3 comprising GYLDPMDY (SEQ ID NO: 5); and a light chain variable region (VL) comprising (i) light chain CDR 1 comprising SASQGINNYLN (SEQ ID NO:12); light chain CDR2 comprising YTSGLHA (SEQ ID NO: 13); and (iii) light chain CDR3 comprising QQYSILPWT (SEQ ID NO: 14); or
f. A heavy chain variable region (VH) comprising (i) heavy chain CDR1 comprising GYTFTSS (amino acids 26-32 of SEQ ID NO:10); (ii) heavy chain CDR2 comprising YPGDGQ (amino acids 52-57 of SEQ ID NO:10); and (iii) heavy chain CDR3 comprising GYLDPMDY (SEQ ID NO: 5); and a light chain variable region (VL) comprising (i) light chain CDR 1 comprising ASQGINNYLN (amino acids 25-34 of SEQ ID NO:16); light chain CDR2 comprising YTSGLHA (SEQ ID NO: 13); and (iii) light chain CDR3 comprising QQYSILPWT (SEQ ID NO: 14).

2. The recombinant host cell of claim 1 wherein the antibody exhibits one or more of the following properties:
   a) a binding affinity ($K_D$) for human IL1RAP of 200 pM or greater;
   b) cross-reactivity with IL1RAP from *Macaca fascicularis;*
   c) an inhibitory action on IL1 signalling;
   d) capability of inducing ADCC in one or more cancer cell lines;
   e) capability of inducing ADCC of cells expressing IL1RAP; and
   f) capability of internalisation upon binding to one or more cancer cell lines.

3. The recombinant host cell of claim 1, wherein the antibody is a Fv fragment or a Fab fragment.

4. The recombinant host cell of claim 1, wherein the antibody or antigen-binding fragment comprises a heavy chain variable region comprising or consisting of the amino acids of SEQ ID NO: 9.

5. The recombinant host cell of claim 1, wherein the antibody or antigen-binding fragment comprises a light chain variable region comprising or consisting of the amino acids of SEQ ID NO: 16.

6. The recombinant host cell of claim 1, wherein the antibody or antigen-binding fragment comprises a heavy chain variable region comprising or consisting of the amino acids of SEQ ID NO: 9 and a light chain variable region comprising or consisting of the amino acids of SEQ ID NO: 16.

7. The recombinant host cell of claim 1 comprising:
   a) a heavy chain variable region which comprises or consists of the amino acid sequence of SEQ ID NO: 8 and a light chain variable region which comprises or consists of the amino acid sequence of SEQ ID NO: 15;
   b) a heavy chain variable region which comprises or consists of the amino acid sequence of SEQ ID NO: 9 and a light chain variable region which comprises or consists of the amino acid sequence of SEQ ID NO: 15;
   c) a heavy chain variable region which comprises or consists of the amino acid sequence of SEQ ID NO: 10 and a light chain variable region which comprises or consists of the amino acid sequence of SEQ ID NO: 15;
   d) a heavy chain variable region which comprises or consists of the amino acid sequence of SEQ ID NO: 11 and a light chain variable region which comprises or consists of the amino acid sequence of SEQ ID NO: 15;
   e) a heavy chain variable region which comprises or consists of the amino acid sequence of SEQ ID NO: 8 and a light chain variable region which comprises or consists of the amino acid sequence of SEQ ID NO: 16;
   f) a heavy chain variable region which comprises or consists of the amino acid sequence of SEQ ID NO: 9 and a light chain variable region which comprises or consists of the amino acid sequence of SEQ ID NO: 16;
   g) a heavy chain variable region which comprises or consists of the amino acid sequence of SEQ ID NO: 10 and a light chain variable region which comprises or consists of the amino acid sequence of SEQ ID NO: 16;
   h) a heavy chain variable region which comprises or consists of the amino acid sequence of SEQ ID NO: 11 and a light chain variable region which comprises or consists of the amino acid sequence of SEQ ID NO: 16;
   i) a heavy chain variable region which comprises or consists of the amino acid sequence of SEQ ID NO: 8 and a light chain variable region which comprises or consists of the amino acid sequence of SEQ ID NO: 17;
   j) a heavy chain variable region which comprises or consists of the amino acid sequence of SEQ ID NO: 9 and a light chain variable region which comprises or consists of the amino acid sequence of SEQ ID NO: 17;
   k) a heavy chain variable region which comprises or consists of the amino acid sequence of SEQ ID NO: 10 and a light chain variable region which comprises or consists of the amino acid sequence of SEQ ID NO: 17; or
   l) a heavy chain variable region which comprises or consists of the amino acid sequence of SEQ ID NO: 11 and a light chain variable region which comprises or consists of the amino acid sequence of SEQ ID NO: 17.

8. The recombinant host cell of claim 1 comprising a heavy and light chain constant region, or part thereof.

9. The recombinant host cell of claim 1 comprising Fc region.

10. The recombinant host cell of claim 1 further comprising a cytotoxic moiety.

11. The recombinant host cell of claim 1 further comprising a detectable moiety.

12. The recombinant host cell of claim 1, wherein the antibody is humanized.

13. The recombinant host cell of claim 1, wherein the antibody or antigen-binding fragment is capable of inducing ADCC of cells expressing IL1RAP.

14. The recombinant host cell of claim 1, wherein the host cell is a bacterial cell.

15. The recombinant host cell of claim 1, wherein the host cell is a mammalian cell.

16. The recombinant host cell of claim 1, wherein the host cell is a human cell.

17. The recombinant host cell of claim 1, wherein the vector is an expression vector.

* * * * *